US010125337B2

(12) United States Patent
Narine et al.

(10) Patent No.: US 10,125,337 B2
(45) Date of Patent: Nov. 13, 2018

(54) BRANCHED DIESTERS AND METHODS OF MAKING AND USING THE SAME

(71) Applicant: TRENT UNIVERSITY, Peterborough (CA)

(72) Inventors: Suresh Narine, Peterborough (CA); Laziz Bouzidi, Peterborough (CA); Latchmi Raghunanan, Peterborough (CA)

(73) Assignee: Trent University, Peterborough, Ontario (CA)

( * ) Notice: Subject to any disclaimer, the term of this patent is extended or adjusted under 35 U.S.C. 154(b) by 0 days.

(21) Appl. No.: 15/352,784

(22) Filed: Nov. 16, 2016

(65) Prior Publication Data

US 2017/0137739 A1   May 18, 2017

Related U.S. Application Data

(60) Provisional application No. 62/255,582, filed on Nov. 16, 2015.

(51) Int. Cl.
*C10M 145/22* (2006.01)
*C10M 129/72* (2006.01)
(Continued)

(52) U.S. Cl.
CPC .......... *C10M 129/72* (2013.01); *C07C 69/67* (2013.01); *C07C 69/675* (2013.01); *C07C 69/73* (2013.01); *C10L 1/191* (2013.01); *C10L 1/1905* (2013.01); *C10L 10/08* (2013.01); *C10M 101/02* (2013.01); *C10M 105/04* (2013.01); *C10M 105/38* (2013.01); *C10M 105/40* (2013.01); *C10M 105/42* (2013.01); *C10M 129/76* (2013.01); *C10L 2200/0476* (2013.01); *C10L 2270/026* (2013.01); *C10M 2203/003* (2013.01); *C10M 2203/022* (2013.01); *C10M 2203/1006* (2013.01); *C10M 2205/0285* (2013.01); *C10M 2207/282* (2013.01); *C10M 2207/283* (2013.01); *C10M 2207/289* (2013.01);
(Continued)

(58) Field of Classification Search
CPC ................ C10M 2209/102; C10M 2209/1023
USPC ................................................. 508/496, 497
See application file for complete search history.

(56) References Cited

U.S. PATENT DOCUMENTS 2,485,160 A    10/1949   Koroly et al.
7,867,959 B2 *  1/2011   Miller .................. C10M 105/36
                                                          508/496
(Continued)

OTHER PUBLICATIONS

Nagendramma, R; Kaul, S., Development of ecofriendly/biodegradable lubricants: An overview. Renewable and Sustainable Energy Reviews 2012, 16, 764-774.
(Continued)

*Primary Examiner* — Ellen M McAvoy
(74) *Attorney, Agent, or Firm* — Bereskin & Parr LLP/S.E.N.C.R.L.; Michael Fenwick

(57) ABSTRACT

The disclosure generally provides branched diester compounds having exceptional low-temperature and flow properties. The disclosure also provides uses of the branched diester compounds in lubricant compositions, for example, as a base oil, and in other applications where their low-temperature and flow properties can be employed beneficially. The disclosure also provides efficient and green methods for making the branched diester compounds.

20 Claims, 11 Drawing Sheets

(51) Int. Cl.
| | |
|---|---|
| C07C 69/67 | (2006.01) |
| C07C 69/73 | (2006.01) |
| C10L 1/19 | (2006.01) |
| C10L 10/08 | (2006.01) |
| C10M 101/02 | (2006.01) |
| C10M 105/04 | (2006.01) |
| C10M 129/76 | (2006.01) |
| C07C 69/675 | (2006.01) |
| C10M 105/38 | (2006.01) |
| C10M 105/40 | (2006.01) |
| C10M 105/42 | (2006.01) |

(52) U.S. Cl.
CPC ............... C10M 2207/2835 (2013.01); C10M 2207/2895 (2013.01); C10M 2207/30 (2013.01); C10M 2207/301 (2013.01); C10M 2209/102 (2013.01); C10M 2209/1023 (2013.01); C10N 2230/02 (2013.01); C10N 2230/64 (2013.01); C10N 2240/02 (2013.01); C10N 2240/04 (2013.01)

(56) References Cited

U.S. PATENT DOCUMENTS

| | | | | |
|---|---|---|---|---|
| 8,188,019 | B2* | 5/2012 | Elomari | B01J 23/26 508/485 |
| 8,741,822 | B2* | 6/2014 | Narine | C10M 105/40 508/463 |
| 9,157,044 | B2* | 10/2015 | Oda | C10M 105/36 |
| 9,683,196 | B2* | 6/2017 | Brekan | C10M 169/042 |
| 2011/0009300 | A1* | 1/2011 | Elomari | C07C 29/132 508/496 |
| 2014/0235517 | A1 | 8/2014 | Narine et al. | |
| 2014/0342959 | A1* | 11/2014 | Miller | C10M 105/36 508/496 |
| 2014/0342960 | A1* | 11/2014 | Miller | C10M 111/02 508/496 |
| 2014/0342961 | A1* | 11/2014 | Miller | C10M 111/02 508/496 |
| 2015/0247104 | A1 | 9/2015 | Brekan et al. | |
| 2016/0046885 | A1* | 2/2016 | Cosimbescu | C10M 145/22 508/466 |

OTHER PUBLICATIONS

Knothe, G.; Steidley, K. R., Lubricity of Components of Biodiesel and Petrodiesel. The Origin of Biodiesel Lubricity. Energy & Fuels 2005, 19, 1192-1200.

Meier, M. A.; Metzger, J. O.; Schubert, U.S. Plant oil renewable resources as green alternatives in polymer science. Chemical Society Reviews 2007, 36, 1788-1802.

Saurabh, T.; Patnaik, M.; Bhagt, S.; Renge, V. Epoxidation of vegetable oils: a review. International Journal of Advanced Engineering Technology 2011, 2, 491-501.

Anastas, R; Eghbali, N. Green Chemistry: Principles and Practice. Chemical Society Reviews 2010, 39:301-312.

Statistica Global production of vegetable oils from 2000/01 to 2014/15 (in million metric tons). http://www.statista.com/statistics/263978/global-vegetable-oil-production-since-2000-2001/ (accessed Sep. 22, 2015).

Mandaković, R. The Key Influences on the Croatian Market of Lubricants and Markets in the Region. goriva i maziva 2011, 50, 307-316.

Tocci, L., Raw Materials under Pressure. Lubes 'n' Greases Mar. 7, 2012, pp. 14-18.

Statistica World production of major vegetable oils from 2000/2001 to 2014/2015, by oil type (in million metric tons). http://www.statista.com/statistics/263933/production-of-vegetable-oils-worldwide-since-2000/ (accessed Sep. 22, 2015).

Schneider, M. P. Plant-oil-based lubricants and hydraulic fluids. Journal of the Science of Food and Agriculture 2006, 86, 1769-1780.

Rodrigues Jr, J. d. A.; Cardoso, F. d. P.; Lachter, E. R.; Estevão, L. R.; Lima, E.; Nascimento, R. S. Correlating chemical structure and physical properties of vegetable oil esters. Journal of the American Oil Chemists' Society 2006, 83, 353-357.

Bouzidi, L.; Li, S.; Di Biase, S.; Rizvi, S. Q.; Narine, S. S. Lubricating and Waxy Esters. 4. Synthesis, Crystallization Behavior, Melt Behavior, and Flow Behavior of Linear Monoesters Incorporating 9-Decenol and 9-Decenoic Acid. Industrial & Engineering Chemistry Research 2013, 52, 2740-2749.

Sharma, B. K.; Erhan, S. Z. 23 Modified Vegetable Oils for Environmentally Friendly Lubricant Applications. Synthetics, Mineral Oils, and Bio-based Lubricants: Chemistry and Technology 2013, 385.

Bouzidi, L.; Li, S.; Di Biase, S.; Rizvi, S. Q.; Dawson, P.; Narine, S. S. Lubricating and Waxy Esters II: Synthesis, crystallization, and Melt Behavior of Branched Monoesters. Industrial & Engineering Chemistry Research 2012, 51, 14892-14902.

Sharma, B. K.; Doll, K. M.; Erhan, S. Z. Ester hydroxy derivatives of methyl oleate: tribological, oxidation and low temperature properties. Bioresource Technology 2008, 99, 7333-7340.

Li, S.; Bouzidi, L.; Narine, S. S. Lubricating and Waxy Esters, V: Synthesis, Crystallization, and Melt and Flow Behaviors of Branched Monoesters Incorporating 9-Decenol and 9-Decenoic Acid. Industrial & Engineering Chemistry Research 2014, 53, 12339-12354.

Hungerford, Z.; Beare, K. D.; Yuen, A. K. L.; Masters, A. F.; Maschmeyer, T. Controlling viscosity in methyl oleate lerivatives through functional group design. New J. Chem. 2014, 38, 5777-5785.

Erhan, S. Z.; Asadauskas, S. Lubricant basestocks from vegetable oils. Industrial Crops and Products 2000, 11, 277-282.

Adhvaryu, A.; Erhan, S. Z.; Perez, J. M. Tribological studies of thermally and chemically modified vegetable oils for use as environmentally friendly lubricants. Wear 2004, 257, 359-367.

Castro, W.; Perez, J. M.; Erhan, S. Z.; Caputo, F. A study of the oxidation and wear properties of vegetable oils: Soybean oil without additives. Journal of the American Oil Chemists Society 2006, 83, 47-52.

Fox, N. J.; Stachowiak, G. W. Vegetable oil-based lubricants—A review of oxidation. Tribology International 2007, 40, 1035-1046.

Lathi, P. S.; Mattiasson, B. Green approach for the preparation of biodegradable lubricant base stock from epoxidized vegetable oil. Applied Catalysis B-Environmental 2007, 69, 207-212.

Sharma, B. K.; Adhvaryu, A.; Liu, Z.; Erhan, S. Z. Chemical modification of vegetable oils for lubricant applications. Journal of the American Oil Chemists' Society 2006, 83, 129-136.

Schmidt, M. A; Dietrich, C. R.; Cahoon, E. B. Biotechnological Enhancement of Soybean Oil for Lubricant Applications. In Synthetics, mineral oils, and bio-based lubricants: chemistry and technology Rudnick, L R., Ed. CRC Press: Boca Raton, FL 2006, 389-398.

Kulkarni, R. D.; Deshpande, P. S.; Mahajan, S. U.; Mahulikar, P. P. Epoxidation of mustard oil and ring opening with 2-ethylhexanol for biolubricants with enhanced thermo-oxidative and cold flow characteristics. Ind. Crop. Prod. 2013, 49, 586-592.

Gamage, P. K.; O'Brien, M.; Karunanayake, L. Epoxidation of some vegetable oils and their hydrolysed products with peroxyformic acid-optimised to industrial scale. Journal of the National Science Foundation of Sri Lanka 2009, 37, 229-240.

Findley, T. W.; Swem, D.; Scanlan, J. T. Epoxidation of unsaturated fatty materials with peracetic acid in glacial acetic acid solution. Journal of the American Chemical Society 1945, 67, 412-414.

Javni, I.; Guo, A.; Petrovic, Z. The study of oxazolidone formation from 9,10-epoxyoctadecane and phenylisocyanate. Journal of the American Oil Chemists' Society 2003, 80, 595-600.

Hong, J.; Luo, Q.; Shah, B. K. Catalyst- and Solvent-Free "Click" Chemistry: A Facile Approach to Obtain Cross-Linked Biopolymers from Soybean Oil. Biomacromolecules 2010, 11, 2960-2965.

Biswas, A.; Sharma, B. K.; Willett, J. L.; Advaryu, K; Erhan, S. Z.; Cheng, H. N. Azide Derivatives of Soybean Oil and Fatty Esters. Journal of Agricultural and Food Chemistry 2008, 56, 5611-5616.

(56) References Cited

OTHER PUBLICATIONS

Anastas, R; Kirchhoff, M. Origins, Current Status, and Future Challenges of Green Chemistry. Accounts of Chemical Research 2002, 35, 686-694.

Li, S.; Bouzidi, L.; Narine, S. S. Lubricating and Waxy Esters. 6. Synthesis and Physical Properties of (E)-Didec-9-enyl Octadec-9-enedioate and Branched Derivatives. Industrial & Engineering Chemistry Research 2014, 53, 20044-20055.

Raghunanan, L; Narine, S. S. Influence of methylene spacer groups on thermal and flow properties of linear aliphatic polyol-derived esters. Journal of Physical Chemistry B (submitted).

Raghunanan, L.; Yue, J.; Narine, S. S. Synthesis and Characterization of Novel Diol, Diacid and Di-isocyanate from Oleic acid. Journal of the American Oil Chemists' Society 2013, (submitted for publication).

Raghunanan, L; Narine, S. S. Influence of Structure on Chemical and Thermal Stability of Aliphatic Diesters. The Journal of Physical Chemistry B 2013, 117, 14754-14762.

Floros, M. C.; Narine, S. S. Latent Heat Storage Using Renewable Phase Change Materials: Saturated Diesters from Vegetable Oils. 2014.

Floros, M. C.; Narine, S. S. Latent Heat Storage Using Renewable Saturated Diesters as Phase Change Materials. Energy (submitted).

Santos, J. C. O.; Santos, I. M. G.; Souza, A. G.; Sobrinho, E. V.; Fernandes, V. J.; Silva, A. J. N. Thermoanalytical and rheological characterization of automotive mineral lubricants after thermal degradation. Fuel 2004, 83, 2393-2399.

Gan, L. H.; Goh, S. H.; Ooi, K. S. Kinetic studies of epoxidation and oxirane cleavage of palm olein methyl esters. Journal of the American Oil Chemists' Society 1992, 69, 347-351.

Campanella, A.; Fontanini, C.; Baltanás, M. A. High yield epoxidation of fatty acid methyl esters with pertormic acid generated in situ. Chemical Engineering Journal 2008, 144, 466-475.

Pillai, P. K. S.; Li, S.; Bouzidi, L; Narine, S. S. Solvent Free Synthesis of Polyols from 1-Butene Metathesized Palm Oil for Use in Polyurethane Foams (unpublished).

Carey, F. A.; Sundberg, R. J., Oxidations. In Advanced Organic Chemistry, Springer: 1990; 615-675.

Parashar, R. K. Reaction mechanisms in organic synthesis. John Wiley & Sons: 2013.

Parker, D. NMR determination of enantiomeric purity. Chemical Reviews 1991, 91, 1441-1457.

Brown, E.; Jaeger, H. M. Through thick and thin. Science 2011, 333, 1230-1231.

Craven, R. J.; Lencki, R. W. Polymorphism of acylglycerols: a stereochemical perspective. Chemical Reviews 2013, 1-13, 7402-7420.

Craven, R. J.; Lencki, R. W. Crystallization, polymorphism, and binary phase behavior of model enantiopure and racemic triacylglycerols. Crystal Growth & Design 2011, 11, 1566-1572.

Craven, R. J.; Lencki, R. W. Crystallization, polymorphism, and binary phase behavior of model enantiopure and racemic triacylglycerols. Crystal Growth & Design 2011, 11, 1723-1732.

Bouzidi, L; Li, S.; Di Biase, S.; Rizvi, S. Q.; Narine, S. S. Lubricating and waxy esters, I. Synthesis, crystallization, and melt behavior of linear monoesters. Chemistry and Physics of Lipids 2012, 165, 38-50.

Debenedetti, P. G.; Stillinger, F. H. Supercooled liquids and the glass transition. Nature 2001, 410, 259-267.

Cermak, S. C.; Bredsguard, J. W.; Roth, K. L.; Thompson, T.; Feken, K. A; Isbell, T. A.; Murray, R. E. Synthesis and 3hysical properties of new coco-oleic estolide branched esters. Industrial Crops and Products 2015, 74, 171-177.

Salimon, J.; Salih, N. Preparation and Characteristic of 9, 10-Epoxyoleic Acid α-Hydroxy Ester Derivatives as Biolubricant Base Oil. European Journal of Scientific Research 2009b, 31, 265-272.

Salimon, J.; Salih, N.; Yousif, E. Chemically modified biolubricant basestocks from epoxidized oleic acid: Improved low temperature properties and oxidative stability. Journal of Saudi Chemical Society 2011a, 15, 195-201.

Salimon, J.; Salih, N.; Abdullah, B. M. Diesters biolubricant base oil: synthesis, optimization, characterization, and physicochemical characteristics. International Journal of Chemical Engineering 2012, 2012.

* cited by examiner

BRANCHED DIESTERS AND METHODS OF MAKING AND USING THE SAME

CROSS-REFERENCE TO RELATED APPLICATIONS

The present application claims the benefit of priority from U.S. provisional application No. 62/255,582 filed on Nov. 16, 2015, the contents of which are incorporated herein by reference in their entirety.

TECHNICAL FIELD

The disclosure generally provides branched diester compounds having exceptional low-temperature and flow properties. The disclosure also provides uses of the branched diester compounds in lubricant compositions, for example, as a base oil, and in other applications where their low-temperature and flow properties can be employed beneficially. The disclosure also provides efficient and green methods for making the branched di ester compounds.

DESCRIPTION OF RELATED ART

Lubricants can be used to reduce friction between surfaces of moving parts and thereby reduce wear and prevent damage to such surfaces and parts. Lubricants are composed primarily of a base stock and one or more lubricant additives. In most instances, the base stock is a relatively high-molecular-weight hydrocarbon. To make lubricants, such as motor oils, transmission fluids, gear oils, industrial lubricating oils, metal working oils, and the like, one can start with a lubricant grade of petroleum oil from a refinery, or a suitable polymerized petrochemical fluid. Into this base stock, small amounts of additive chemicals are blended to improve material properties and performance, such as enhancing lubricity, inhibiting wear and corrosion of metals, and retarding damage to the fluid from heat and oxidation. As such, various additives such as oxidation and corrosion inhibitors, dispersing agents, high pressure additives, anti-foaming agents, metal deactivators, and other additives suitable for use in lubricant formulations, can be added in conventional effective quantities.

In some instances, however, it can be undesirable to employ base stocks composed only of hydrocarbons. This is especially true in applications where there is a large amount of pressure applied to moving parts, where such compositions tend to fail, and the parts become damaged. In such instances, one can use synthetic esters, which can be used either as a base stock or, in smaller quantities, as an additive. By comparison with the less expensive, but environmentally less safe mineral oils, synthetic esters can be used as base oils in cases where the viscosity or temperature behavior is expected to be placed under stringent demands. Further, the increasingly important issues of environmental acceptance and biodegradability are the drivers behind the desire for alternatives to mineral oil as a base stock in lubricating applications.

Examples of synthetic esters include polyol esters and triglycerides found in natural oils. Of key importance to natural oil-derived lubricants are physical properties, such as improved low-temperature properties, improved viscosity at the full range of operating conditions, improved oxidative stability (meaning removal of any carbon-carbon double bonds in the case of natural oil-derived materials), and improved thermal stability.

One class of ester lubricants includes the glycerol esters found in various natural oils (e.g., seed oils or vegetable oils), and derivative synthesized therefrom. Natural oils contain a large and diverse group of molecules comprised predominantly of triacylglycerols (TAGs) (>95%) and which possess inherent biodegradability and lubricity. They are abundant renewable, non-toxic and non-volatile materials suitable as feedstock for the development of environmentally adapted materials, including lubricants, according to the principles of green chemistry. In 2012-2013, for example, the global production of natural oils was approximately 161 MMT—four times that of the production of the global lubricants industry—and of which some 50% was from unsaturated fatty acid-rich oilseed crops (e.g., soybean, canola, and sunflower oils).

One of the largest limitation of TAG molecules to their potential applications in lubricant formulations is poor flow performance at subzero temperatures. Transforming vegetable oils into linear aliphatic molecules analogous to well-established synthetic ester analogues currently available in the marketplace is one of the approaches employed to mitigate this shortcoming. Such transformations are facilitated by the conversion of TAGs into their constituent fatty acids or fatty acid esters via hydrolysis or esterification, respectively. This approach is advantageous in that it allows the syntheses of materials which can access a wider viscosity range and lubricity than native vegetable oils. The low temperature flow performance of vegetable oil-based materials may be further improved by increasing unsaturation, introducing molecular asymmetry via varying ester group and double bond positions, control of double bond configuration, and with the introduction of branched groups. Of these, branching has been the most favored because of the increase in oxidative stability which accompanies the removal of the unsaturated carbon-carbon double bonds. Branches can be introduced at the double bond positions via chemical reactions such as epoxidation, acylation, and etherification.

Epoxidation can be used to introduce functional groups onto an olefin. The mechanism occurs via the concerted addition of a peracid, generated in situ or prepared in advance, to the weakly nucleophilic double bond of the olefin. Typical peracids used in the epoxidation of fatty acid esters and related derivatives include performic acid, perchlorobenzoic acid and peracetic acid. According to the principles of green chemistry, performic acid is preferred as it is the least toxic and least corrosive. Subsequent ring opening of the epoxide with an appropriate nucleophile, e.g. fatty acids or alcohols, gives the desired α-hydroxy branched derivative.

Such chemistries have been used in various ways to make synthetic esters from natural oils that have properties that may make them more suitable for use as a lubricant than the TAGs themselves. For example, at the Trent Centre for Biomaterials Research (TCBR), several series of branched ester derivatives have been prepared via a green one-pot approach which included the solvent- and catalyst-free ring opening reaction of ester epoxides with propanoic acid followed by in situ normal esterification of the α-hydroxy group. See, for example, U.S. Pat. No. 8,741,822 of Narine et al., which is incorporated herein by reference, and which discloses various branched polyester derivatives of linear lipid-based monoesters and a diacid diester. These compounds demonstrated a wide range of viscosity and suppression of crystallization down to −90° C., but were limited by the positional isomerism of the terminal branched groups, such that the non-protuberant branches resulted in strong crystallization from the melt. Further, U.S. Patent Application Publication No. 2015/0247104, of Brekan et al., discloses branched diesters for use in lubricant formulations, wherein the branched groups are hydrocarbon branches. Such branched diesters possess excellent low-temperature performance, but generally have a low viscosity (e.g., 2.8 to 8.1 cSt at 100° C.).

Thus, there is a continuing need to develop new synthetic esters that can simultaneously exhibit higher viscosities and desirable low-temperature performance.

SUMMARY

The novel diesters disclosed herein overcome one or more of these challenges by providing compounds that have high viscosity and possess exceptional low-temperature performance. In certain embodiments, the branched groups in the functionally branched derivatives disclosed herein are internal and, therefore, protuberant, resulting in suppression of crystallization regardless of the isomeric inhomogeneity of the derivatives (glass transitions occurred below −65° C.). Furthermore, in certain embodiments, the polar ester branches and the presence of OH groups—a consequence of the synthetic approach used to prepare these materials—result in a large range of viscosity for the branched derivatives of this work (162-338 mPa·s at 40° C. and 24-36 mPa·s at 100° C.). In certain embodiments, the branched derivatives disclosed herein possess inherently improved oxidative stability due to the removal of the double bonds. The low temperature performance and viscosity of the functionally branched diester derivatives make them suitable for use as high performance lubricants including, but not limited to, industrial gear and bearing oils.

In a first aspect, the disclosure provides compounds of formula (I):

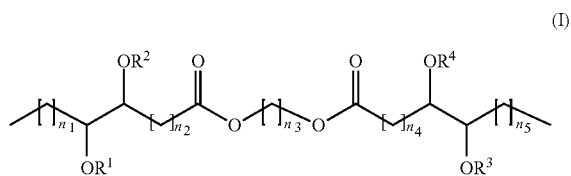

wherein: $R^1$, $R^2$, $R^3$, and $R^4$ are independently a hydrogen atom or —C(O)—($C_{1-6}$ alkyl); $n_1$ and $n_5$ are independently an integer from 5 to 13; $n_2$ and $n_4$ are independently an integer from 6 to 13; and $n_3$ is an integer from 2 to 10. In some embodiments, $n_1$, n2, $n_4$, and $n_5$ are 7, and $n_3$ is 6. In some further such embodiments, at least two of $R^1$, $R^2$, $R^3$, and $R^4$ are —C(O)—($C_{1-6}$ alkyl), such as —C(O)—$CH_2CH_3$.

In a second aspect, the disclosure provides compositions comprising one or more compounds of the first aspect. In some embodiments, the composition is a lubricant composition, such as a gear oil. In some other embodiments, the composition is a fuel composition, such as a biodiesel composition.

In a third aspect, the disclosure provides methods of lubricating a surface, comprising: providing a first surface and a second surface, which are in physical contact with each other; and contacting the first surface and the second surface with a composition of the second aspect at a point where the surfaces are in physical contact with each other.

In a fourth aspect, the disclosure provides methods of making branched diester compounds, the method comprising: providing (i) a short-chain diol, and (ii) an unsaturated fatty acid, or an ester thereof; reacting the short-chain diol with the unsaturated fatty acid, or the ester thereof, to form a diester comprising two unsaturated fatty acid moieties; epoxidizing one or more of the carbon-carbon double bonds of the unsaturated fatty acid moieties of the diester to form an epoxidized diester; and reacting the epoxidized diester with a short-chain carboxylic acid, or an ester thereof, to form a branched diester.

Further aspects and embodiments are disclosed in the Detailed Description.

BRIEF DESCRIPTION OF THE DRAWINGS

The following drawings are provided for purposes of illustrating various embodiments of the compounds, compositions, and methods disclosed herein. The drawings are provided for illustrative purposes only, and are not intended to describe any preferred compounds, preferred compositions, or preferred methods, or to serve as a source of any limitations on the scope of the claimed inventions.

DETAILED DESCRIPTION

Figure 1:
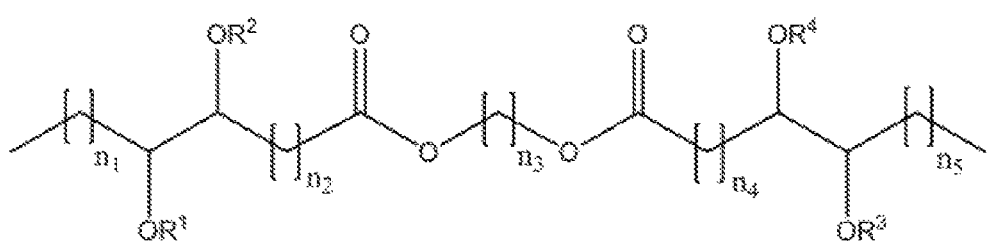
FIG. 1 shows an embodiment of certain branched diesters disclosed herein, wherein $R^1$, $R^2$, $R^3$, and $R^4$ are independently a hydrogen atom or —C(O)—($C_{1-6}$ alkyl); $n_1$ and $n_5$ are independently an integer from 5 to 13; $n_2$ and $n_4$ are independently an integer from 6 to 13; and $n_3$ is an integer from 2 to 10.

The following description recites various aspects and embodiments of the inventions disclosed herein. No particular embodiment is intended to define the scope of the invention. Rather, the embodiments provide non-limiting examples of various compositions, and methods that are included within the scope of the claimed inventions. The description is to be read from the perspective of one of ordinary skill in the art. Therefore, information that is well known to the ordinarily skilled artisan is not necessarily included.

Definitions

The following terms and phrases have the meanings indicated below, unless otherwise provided herein. This disclosure may employ other terms and phrases not expressly defined herein. Such other terms and phrases shall have the meanings that they would possess within the context of this disclosure to those of ordinary skill in the art. In some instances, a term or phrase may be defined in the singular or plural. In such instances, it is understood that any term in the singular may include its plural counterpart and vice versa, unless expressly indicated to the contrary.

As used herein, the singular forms "a," "an," and "the" include plural referents unless the context clearly dictates otherwise. For example, reference to "a substituent" encompasses a single substituent as well as two or more substituents, and the like.

As used herein, "for example," "for instance," "such as," or "including" are meant to introduce examples that further clarify more general subject matter. Unless otherwise expressly indicated, such examples are provided only as an aid for understanding embodiments illustrated in the present disclosure, and are not meant to be limiting in any fashion. Nor do these phrases indicate any kind of preference for the disclosed embodiment.

As used herein, "reaction" and "reacting" refer to the conversion of a substance into a product, irrespective of reagents or mechanisms involved.

The terms "group" or "moiety" refers to a linked collection of atoms or a single atom within a molecular entity, where a molecular entity is any constitutionally or isotopically distinct atom, molecule, ion, ion pair, radical, radical ion, complex, conformer etc., identifiable as a separately distinguishable entity.

As used herein, "mix" or "mixed" or "mixture" refers broadly to any combining of two or more compositions. The two or more compositions need not have the same physical state; thus, solids can be "mixed" with liquids, e.g., to form a slurry, suspension, or solution. Further, these terms do not require any degree of homogeneity or uniformity of composition. This, such "mixtures" can be homogeneous or heterogeneous, or can be uniform or non-uniform. Further, the terms do not require the use of any particular equipment to carry out the mixing, such as an industrial mixer.

As used herein, the term "natural oil" refers to oils derived from various plants or animal sources. These terms include natural oil derivatives, unless otherwise indicated. The terms also include modified plant or animal sources (e.g., genetically modified plant or animal sources), unless indicated otherwise. Examples of natural oils include, but are not limited to, vegetable oils, algae oils, fish oils, animal fats, tall oils, derivatives of these oils, combinations of any of these oils, and the like. Representative non-limiting examples of vegetable oils include rapeseed oil (canola oil), coconut oil, corn oil, cottonseed oil, olive oil, palm oil, peanut oil, safflower oil, sesame oil, soybean oil, sunflower oil, linseed oil, palm kernel oil, tung oil, jatropha oil, mustard seed oil, pennycress oil, camelina oil, hempseed oil, and castor oil. Representative non-limiting examples of animal fats include lard, tallow, poultry fat, yellow grease, and fish oil. Tall oils are by-products of wood pulp manufacture. In some embodiments, the natural oil or natural oil feedstock comprises one or more unsaturated glycerides (e.g., unsaturated triglycerides).

As used herein, "natural oil derivatives" refers to the compounds or mixtures of compounds derived from a natural oil using any one or combination of methods known in the art. Such methods include but are not limited to saponification, fat splitting, transesterification, esterification, hydrogenation (partial, selective, or full), isomerization, oxidation, and reduction. Representative non-limiting examples of natural oil derivatives include gums, phospholipids, soapstock, acidulated soapstock, distillate or distillate sludge, fatty acids and fatty acid alkyl ester (e.g. non-limiting examples such as 2-ethylhexyl ester), hydroxy substituted variations thereof of the natural oil. For example, the natural oil derivative may be a fatty acid methyl ester ("FAME") derived from the glyceride of the natural oil.

As used herein, "alkyl" refers to a straight or branched chain saturated hydrocarbon having 1 to 30 carbon atoms, which may be optionally substituted, as herein further described, with multiple degrees of substitution being allowed. Examples of "alkyl," as used herein, include, but are not limited to, methyl, ethyl, n-propyl, isopropyl, isobutyl, n-butyl, sec-butyl, tert-butyl, isopentyl, n-pentyl, neopentyl, n-hexyl, and 2-ethylhexyl. The number carbon atoms in an alkyl group is represented by the phrase "$C_{x-y}$ alkyl," which refers to an alkyl group, as herein defined, containing from x to y, inclusive, carbon atoms. Thus, "$C_{1-6}$ alkyl" represents an alkyl chain having from 1 to 6 carbon atoms and, for example, includes, but is not limited to, methyl, ethyl, n-propyl, isopropyl, isobutyl, n-butyl, sec-butyl, tert-butyl, isopentyl, n-pentyl, neopentyl, and n-hexyl.

As used herein, the term "short-chain diol" refers to an aliphatic alcohol having from 1 to 12 carbon atoms and two or more OH groups. Non-limiting examples include ethylene glycol, propylene glycol (1,2 and 1,3), etc. In some embodiments, the short-chain diol has exactly two OH groups. In some embodiments, the short-chain diol is saturated and/or acyclic.

As used herein, the term "unsaturated fatty acid" refers to a carboxylic acid compound having one or more carbon-carbon double bonds derived from a natural oil, as defined herein. Non-limiting examples include oleic acid, linoleic acid, linolenic acid, etc.

As used herein, the term "short-chain carboxylic acid" refers to an aliphatic carboxylic acid having from 2 to 12 carbon atoms. Non-limiting examples include acetic acid, propanoic acid, butyric acid, etc. In some embodiments, the short-chain carboxylic acid is saturated (except for the carbonyl bond of the acid group). In some embodiments, the short-chain carboxylic acid is acyclic.

As used herein, "comprise" or "comprises" or "comprising" or "comprised of" refer to groups that are open, meaning that the group can include additional members in addition to those expressly recited. For example, the phrase, "comprises A" means that A must be present, but that other members can be present too. The terms "include," "have," and "composed of" and their grammatical variants have the same meaning. In contrast, "consist of" or "consists of" or "consisting of" refer to groups that are closed. For example, the phrase "consists of A" means that A and only A is present.

As used herein, "or" is to be given its broadest reasonable interpretation, and is not to be limited to an either/or construction. Thus, the phrase "comprising A or B" means that A can be present and not B, or that B is present and not A, or that A and B are both present. Further, if A, for example, defines a class that can have multiple members, e.g., A1 and A2, then one or more members of the class can be present concurrently.

As used herein, the various functional groups represented will be understood to have a point of attachment at the functional group having the hyphen or dash (-) or an asterisk (*). In other words, in the case of —$CH_2CH_2CH_3$, it will be understood that the point of attachment is the $CH_2$ group at the far left. If a group is recited without an asterisk or a dash, then the attachment point is indicated by the plain and ordinary meaning of the recited group.

In some instances herein, organic compounds are described using the "line structure" methodology, where chemical bonds are indicated by a line, where the carbon atoms are not expressly labeled, and where the hydrogen atoms covalently bound to carbon (or the C—H bonds) are not shown at all. For example, by that convention, the formula  represents n-propane.

As used herein, multi-atom bivalent species are to be read from left to right. For example, if the specification or claims recite A-D-E and D is defined as —OC(O)—, the resulting group with D replaced is: A-OC(O)-E and not A-C(O)O-E.

Unless a chemical structure expressly describes a carbon atom as having a particular stereochemical configuration, the structure is intended to cover compounds where such a stereocenter has an R or an S configuration.

Other terms are defined in other portions of this description, even though not included in this subsection.

Branched Diester Compounds

In at least one aspect, the disclosure provides branched diester compounds formed from a short-chain diol and unsaturated fatty acids (or esters thereof). In some embodiments, the branched diester compounds are compounds of formula (I):

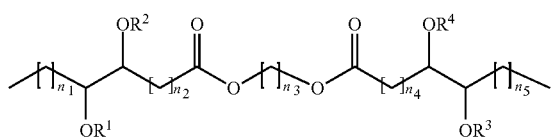

(I)

wherein: $R^1$, $R^2$, $R^3$, and $R^4$ are independently a hydrogen atom or —C(O)—($C_{1-6}$ alkyl); $n_1$ and $n_5$ are independently an integer from 5 to 13; $n_2$ and $n_4$ are independently an integer from 6 to 13; and $n_3$ is an integer from 2 to 10. In some embodiments, $n_1$, $n_2$, $n_4$, and $n_5$ are 7, and $n_3$ is 6. In some further such embodiments, at least two of $R^1$, $R^2$, $R^3$, and $R^4$ are —C(O)—($C_{1-6}$ alkyl), such as —C(O)—$CH_2CH_3$.

In some embodiments, $R^1$ is a hydrogen atom. In some other embodiments, $R^1$ is a —C(O)—($C_{1-6}$ alkyl) moiety, such as —C(O)—$CH_2CH_3$. In some embodiments of any of the foregoing embodiments, $R^2$ is a hydrogen atom. In some other embodiments of any of the foregoing embodiments, $R^2$ is a —C(O)—($C_{1-6}$ alkyl) moiety, such as —C(O)—$CH_2CH_3$. In some embodiments of any of the foregoing embodiments, $R^3$ is a hydrogen atom in some other embodiments of any of the foregoing embodiments, $R^3$ is a C(O)—($C_{1-6}$ alkyl) moiety, such as —C(O)—$CH_2CH_3$. In some embodiments of any of the foregoing embodiments, $R^4$ is a hydrogen atom. In some other embodiments of any of the foregoing embodiments, $R^4$ is a —C(O)—($C_{1-6}$ alkyl) moiety, such as —C(O)—$CH_2CH_3$. In some embodiments, one of $R^1$, $R^2$, $R^3$, and $R^4$ is a hydrogen atom. In some embodiments, one of $R^1$, $R^2$, $R^3$, and $R^4$ is —C(O)—($C_{1-6}$ alkyl). In some embodiments, one of $R^1$, $R^2$, $R^3$, and $R^4$ is —C(O)—$CH_2CH_3$.

In some of the foregoing embodiments, the compounds can be fully acylated (i.e., none of $R^1$, $R^2$, $R^3$, and $R^4$ is a hydrogen atom) or partially acylated (i.e., one, two, or three of $R^1$, $R^2$, $R^3$, and $R^4$ are acylated). In some such embodiments, no more than two of $R^1$, $R^2$, $R^3$ and $R^4$ are a hydrogen atom. In some other such embodiments, no more than one of $R^1$, $R^2$, $R^3$, and $R^4$ is a hydrogen atom. In some other such embodiments, none of $R^1$, $R^2$, $R^3$, and $R^4$ is a hydrogen atom.

In some embodiments, exactly two of $R^1$, $R^2$, $R^3$, and $R^4$ are acylated and exactly two are a hydrogen atom. Such compounds may be referred to herein as "two-branched" diesters. In such embodiments, any two of $R^1$, $R^2$, $R^3$, and $R^4$ are acylated. For example, in some embodiments, $R^1$ and $R^2$, or $R^1$ and $R^3$, or $R^1$ and $R^4$, or $R^2$ and $R^3$, or $R^2$ and $R^4$, or $R^3$ and $R^4$, are acylated, while, in each case, the remaining positions are a hydrogen atom.

In some embodiments, exactly three of $R^1$, $R^2$, $R^3$, and $R^4$ are acylated and exactly one is a hydrogen atom. Such compounds may be referred to herein as "three-branched" diesters. In such embodiments, any three of $R^1$, $R^2$, $R^3$, and $R^4$ are acylated. For example, in some embodiments, $R^1$, $R^2$, and $R^3$, or $R^1$, $R^2$, and $R^4$, or $R^1$, $R^3$, and $R^4$, or $R^2$, $R^3$, and $R^4$, are acylated, while, in each case, the remaining position is a hydrogen atom.

In some embodiments, all of $R^1$, $R^2$, $R^3$, and $R^4$ are acylated and none is a hydrogen atom. Such compounds may be referred to herein as "four-branched" diesters.

The value of $n_3$ depends on the diol used to make the diester. For example, in some embodiments of any of the foregoing embodiments, $n_3$ is 1, 2, 3, 4, 5, 6, 7, 8, 9, or 10. In some such embodiments, $n_3$ is 2, 4, 6, 8, or 10. In some further such embodiments, $n_3$ is 4, 6, or 8. In some even further such embodiments, $n_3$ is 6.

The values of $n_1$, $n_2$, $n_4$, and $n_5$ depend on the nature of the unsaturated fatty acid used to make the branched diester. In some embodiments of any of the aforementioned embodiments, $n_2$ is 6, 7, 8, 9, 10, 11, 12, or 13. In some such embodiments, $n_2$ is 7, 9, 11, or 13. In some further such embodiments, $n_2$ is 7. In some embodiments of any of the aforementioned embodiments, $n_4$ is 6, 7, 8, 9, 10, 11, 12, or 13. In some such embodiments, $n_4$ is 7, 9, 11, or 13. In some further such embodiments, $n_4$ is 7. In some embodiments of any of the aforementioned embodiments, $n_1$ is 5, 6, 7, 8, 9, 10, 11, 12, or 13. In some such embodiments, $n_1$ is 5, 7, 9, or 11. In some further such embodiments, $n_1$ is 5 or 7. In some even further such embodiments, $n_1$ is 7. In some embodiments of any of the aforementioned embodiments, $n_5$ is 5, 6, 7, 8, 9, 10, 11, 12, or 13. In some such embodiments, $n_5$ is 5, 7, 9, or 11. In some further such embodiments, $n_5$ is 5 or 7. In some even further such embodiments, $n_5$ is 7.

The branched diesters disclosed herein can be synthesized by any suitable means, although some means may be more desirable than others. Suitable synthetic methodologies are disclosed in the Examples, below. The claims to the compounds, or to compositions including the compounds, are not limited in any way by the synthetic method used to make the compounds.

In certain aspects, the disclosure provides methods of making branched diester compounds, the method comprising: providing (i) a short-chain diol, and (ii) an unsaturated fatty acid, or an ester thereof reacting the short-chain diol with the unsaturated fatty acid, or the ester thereof, to form a diester comprising two unsaturated fatty acid moieties; epoxidizing one or more of the carbon-carbon double bonds of the unsaturated fatty acid moieties of the diester to form an epoxidized diester; and reacting the epoxidized diester with a short-chain carboxylic acid, or an ester thereof, to form a branched diester.

Any suitable short-chain diol can be used. In some embodiments, the short-chain diol is a $C_{2-10}$ diol. In some such embodiments, the short-chain diol is ethylene glycol, 1,3-propylene glycol, 1,4-butanediol, 1,5-pentanediol, 1,6-hexanediol, 1,7-heptanediol, 1,8-octanediol, 1,9-nonanediol, or 1,10-decanediol. In some such embodiments, the short-chain diol is 1,6-hexanediol. Further, any suitable unsaturated fatty acid, or ester thereof, can be used. In some embodiments, the unsaturated fatty acid, or the ester thereof, is a monounsaturated fatty acid, or an ester thereof. In some such embodiments, the unsaturated fatty acid, or the ester thereof, is nervonic acid, erucic acid, gondoic acid, oleic acid, elaidic acid, palmitoleic acid, or any esters thereof. In some further such embodiments, the unsaturated fatty acid is oleic acid, or an ester thereof. In embodiments where a fatty acid ester is employed, the esters can be any suitable ester, such as $C_{1-6}$ alkyl esters, e.g., methyl esters, ethyl esters, isopropyl esters, etc. The reaction of the diol with the unsaturated fatty acid or unsaturated fatty acid ester can be carried out by any suitable method for making esters.

The epoxidation can be carried out by any suitable epoxidation method. In certain embodiments, however, the epoxidation is carried out by methods describes below in the section entitled "Preparation of Branched Di esters," which is incorporated herein by reference.

In some such embodiments, the epoxide ring is opened by reacting the epoxidized diester with one or more compounds that include a short-chain carboxylic acid, or an ester thereof. In some embodiments, the short-chain carboxylic acid, or the ester thereof is a $C_{2-6}$ carboxylic acid, or an ester thereof. In some further embodiments, the short-chain carboxylic acid, or the ester thereof, is propanoic acid, or an ester thereof. In some embodiments, the ring-opening is carried out using a green solvent-free method, such that the reacting of the epoxidized diester is carried out in the substantial absence of an organic solvent. In this context, the term "substantial absence" means that the reaction mixture includes no more than 10% by weight, or no more than 5% by weight, or no more than 3% by weight, or no more than 1% by weight, of an organic solvent, such as dichloromethane.

Compositions Including Branched Diesters

In certain aspects, the disclosure provides various compositions including branched diester compounds of any of the foregoing embodiments. Such compositions can include the branched diester compounds in any suitable quantity. Moreover, the compositions can include two or more branched diester compounds having different molecular structures or different isomeric relationships with respect to each other.

As noted above, various branched diester compounds can be classified according to their degree of acylation at $R^1$, $R^2$, $R^3$, and $R^4$, according to formula (I), above, A "two-branched" diester refers to a diester that is acylated exactly twice; a "three-branched" diester refers to a diester that is acylated exactly three times; and a "four-branched" diester refers to a diester that is acylated exactly four times. In certain embodiments, the compositions include combinations of two-branched, three-branched, and four-branched diesters.

For example, in some embodiments, composition includes a first compound of formula (I), wherein $R^1$, $R^2$, $R^3$, and $R^4$ are —C(O)—($C_{1-6}$ alkyl); a second compound of formula (I), wherein one of $R^1$, $R^2$, $R^3$, and $R^4$ is a hydrogen atom, and the other three of $R^1$, $R^2$, $R^3$, and $R^4$ are —C(O)—($C_{1-6}$ alkyl); and a third compound of formula (I), wherein two of $R^1$, $R^2$, $R^3$, and $R^4$ are a hydrogen atom, and the other two of $R^1$, $R^2$, $R^3$, and $R^4$ are —C(O)—($C_{1-6}$ alkyl). In some such embodiments, the composition includes a first compound of formula (I), wherein $R^1$, $R^2$, $R^3$, and $R^4$ are —C(O)—CH$_2$CH$_3$; a second compound of formula (I), wherein one of $R^1$, $R^2$, $R^3$, and $R^4$ is a hydrogen atom, and the other three of $R^1$, $R^2$, $R^3$, and $R^4$ are —C(O)—CH$_2$CH$_3$; and a third compound of formula (I), wherein two of $R^1$, $R^2$, $R^3$, and $R^4$ are a hydrogen atom, and the other two of $R^1$, $R^2$, $R^3$, and $R^4$ are —C(O)—CH$_2$CH$_3$.

In certain embodiments, the compositions disclosed herein have certain desirable low-temperature properties. For example, in some embodiments, the composition has a glass transition temperature ($T_g$) of no more than −65° C.

In certain embodiments, the compositions disclosed herein have a desirable viscosity at relevant temperatures. For example, in some embodiments, the viscosity of the composition at 40° C. is at least 160 cP. In some embodiments, the viscosity of the composition at 100° C. is at least 24 cP.

Such compositions can be used in a wide array of applications, including, but not limited to, lubricant compositions (e.g., oil for gears or bearings), biodiesel compositions (e.g., for suppression of crystallization), and plasticizer compositions (e.g., for plasticizing PVC or PVB).

In some embodiments, the compositions are lubricant compositions, such as a gear oil composition. In some such embodiments, the lubricant composition is a gear oil, such as a GL-4 gear oil or a GL-5 gear oil. In some such embodiments, the branched diesters are blended with one or more other base oils. Non-limiting examples include, but are not limited to, mineral oil or a polyalpha-olefin). In some such embodiments, the branched diester compounds make up from 1 to 70 percent by weight, or from 1 to 50 percent by weight, or from 1 to 30 percent by weight, of the lubricant composition, based on the total weight of the finished lubricant composition.

In some such embodiments, the lubricant composition includes one or more additives. Such additives include, but are not limited to, dispersants, detergents, anti-wear agents, antioxidants, metal deactivators, extreme pressure (EP) additives, viscosity modifiers such as viscosity index improvers, pour point depressants, corrosion inhibitors, friction coefficient modifiers, colorants, antifoam agents, antimisting agents, demulsifiers, organomolybdenum compounds, and zinc dialkyl dithiophosphates. In some embodiments, for example, where the lubricant composition is blended to be suitable for use as a gear oil, the lubricant composition includes a standard additive package, such as an additive package for a GL-4 or GL-5 gear oil.

The one or more additives can be used in any suitable amount in the lubricant composition. The quantity and combination of additives used can depend on a variety of factors, including, but not limited to, the properties of the base oil, the properties of the selected additives, and the desired properties of the resulting composition. In some embodiments, the one or more additives make up from 0.1 to 50 weight percent, or from 0.1 to 40 weight percent, or from 0.1 to 30 weight percent, or from 0.1 to 20 weight percent, or from 0.1 to 15 weight percent.

Consistent with the use of the compositions disclosed herein as lubricant compositions, the compositions can be employed in a lubrication method. For example, in certain aspects, the disclosure provides methods of lubricating a surface, comprising: providing a first surface and a second surface, which are in physical contact with each other; and contacting the first surface and the second surface with a composition of any one of foregoing embodiments at a point where the surfaces are in physical contact with each other. In some embodiments, at least one of the first surface or the second surface is the surface of a gear or bearing.

In some other aspects and embodiments, the composition is a fuel composition, such as a biodiesel composition. In some such embodiments, the diester compounds make up from 1 to 20 percent by weight, or from 1 to 10 percent by weight, or from 1 to 5 percent by weight, of the fuel composition, based on the total weight of the fuel composition.

EXAMPLES

The following examples are provided to illustrate one or more preferred embodiments of the invention. Numerous variations can be made to the following examples that lie within the scope of the claimed inventions.

Materials and Methods
Materials

Formic acid (88 wt %), hydrogen peroxide solution (30 wt %), propanoic acid (≥98%) and anhydrous sodium sulphate (99.4%) were purchased from Sigma-Aldrich Co. (USA). Acetone, dichloromethane (DCM), ethyl acetate, and hexanes were purchased from ACP Chemical Int, (Montreal, Quebec, Canada). Silica gel (230-400 mesh) was obtained from Rose Scientific Ltd (AB, Canada). TLC plates (250 μm) were obtained from Silicycle Chemistry Division (QC, Canada). All materials were used as purchased unless otherwise specified.

The base diester, 6-(oleoyloxy)hexyloleate (18-6-18), used in the preparation of the branched derivatives was prepared in our laboratory in high yield from an oleic acid derivative and 1,6-hexanediol. The preparation and properties of 18-6-18 were reported previously.

Analytical Methods
  Chemical Characterization
  1H-Nuclear Magnetic Resonance
  1-Dimensional $^1$H-NMR was obtained using a Varian VNMR spectrometer [υ(1H)=399.75 MHz; Varian Inc., Walnut Creek, Calif., USA] equipped with a 5-mm PRF auto switchable $^1$H probe. Samples were dissolved in approximately 2 mL CDCl$_3$ and run at 25° C. over a 30,000 Hz spectral window with a 1 second recycle delay. The spectra were collected over 16 transients and zero-filled to 32 K complex points.
  Mass Spectroscopy
  Electrospray ionization mass spectrometry (ESI-MS) was performed on an API 3000 triple quadrupole mass spectrometer (PE Sciex) equipped with an electron ionspray source (ESI). The ion source and interface conditions were adjusted as follows: ionspray voltage (IS)=5500V, nebulising gas (GS1)=8, curtain gas (GS2)=8, entrance potential (EP)=15 V, focusing potential (FP)=330, declustering potential (DP)=80 V, and HSID temperature=0° C. Samples (1 ppm (wt/vol)) were prepared using chloroform-acetonitrile 10:90(v/v). All samples were injected by direct infusion at a flow of 10 μL/min. Ion signals were reconstructed using the Analyst 1.6.2 software package (AB Sciex, Concord, ON).
  High Performance Liquid Chromatography
  HPLC measurements were carried out on a Waters Alliance (Milford, Mass.) e2695 HPLC system fitted with a Waters ELSD 2424 evaporative light scattering detector (ELSD). The system included an inline degasser, a pump, and an auto-sampler. A 150×4.6 mm XBridge C18 column (5 μm average particle size, Waters Limited, Mississauga, ON) was used in the reversed-phase isocratic mode. The temperature of the column was maintained at 35° C. The ELSD nitrogen pressure was set at 25 psi and the nebulizer set to cooling mode. The drift tube temperature was maintained at 55° C. Gain was set at 500. Samples were prepared by dissolving in chloroform (1 mg/mL). Samples were run for 30 min at a flow rate of 0.5 ml/min using a mobile phase of chloroform:acetonitrile (10:90 v/v). Sample size was 10 μL. Chloroform and acetonitrile were HPLC grade and obtained from VWR International, Mississauga, ON. The Waters Empower Version 2 software was used for data collection and data analysis.
  Physical Characterization
  Differential Scanning Calorimetry (DSC)
  DSC measurements were carried out on a Q200 model (TA instruments, New Castle, Del., USA) under a nitrogen flow of 50 mL/min. Samples (5.5±1.0 mg) were placed in hermetically sealed aluminum DSC pans and equilibrated at 70° C. for 5 min to remove thermal history. The cooling profile was subsequently obtained by cooling the sample to −90° C. at 3° C./min, and the heating profile obtained upon heating at 3° C./min to 70° C. following equilibration at −90° C. for 5 min. The data were analyzed using the 'TA Universal Analysis' software. The thermal values and uncertainties attached are the average and standard deviation, respectively, of at least three runs.
  Rheology
  Flow and viscosity properties of the diesters were measured on an AR2000ex computer-controlled rheometer (TA instruments) using a 40-mm 2° steel cone geometry. Temperature control was achieved by Peltier thermoelectric regulation to better than 0.2° C.

Flow behavior was determined from shear rate-shear stress experiments using the steady state procedure. Shear stress was measured as a function of shear rate between 1-1200 s$^{-1}$ at selected temperatures between 100 and 0° C., inclusive. The system was allowed to come to equilibrium for 5 minutes before each measurement. Data points were recorded at 1-minute intervals to give a total of 50 sample points per experiment. Flow behavior was modelled using both the Herschel-Bulkley (Eqn. 1) and the Ostwald (Eqn. 2) equations. The former describes the behavior of fluids which flow with a yield stress. In the absence of a yield stress, the Herschel Bulkley model transforms into the Ostwald model, from which viscosity can be derived:

$$\tau = \tau° + \kappa \cdot \gamma^a \quad \text{Eqn. 1}$$

$$\tau = \eta \cdot \gamma^a \quad \text{Eqn. 2}$$

where τ=shear stress in Pa, κ=consistency index, η=viscosity in Pa·s, γ=shear rate in s$^{-1}$, τ°=yield stress in Pa, and a=flow behavior index. When a=1, fluids are Newtonian (i.e., viscosity is constant over all shear), and κ=η. When a<1 and a>1, fluids are shear thinning and shear thickening, respectively.

The viscosity versus temperature data were collected using the constant temperature rate method with a shear rate of 200 s-1. The samples were quickly heated to 110° C. and equilibrated at this temperature for 5 minutes then cooled down to 0° C. at a constant rate of 3.0° C./min. Data points were recorded at 1° C. intervals to give a total of 110 points per run.

Preparation of Branched Diesters

Figure 2:
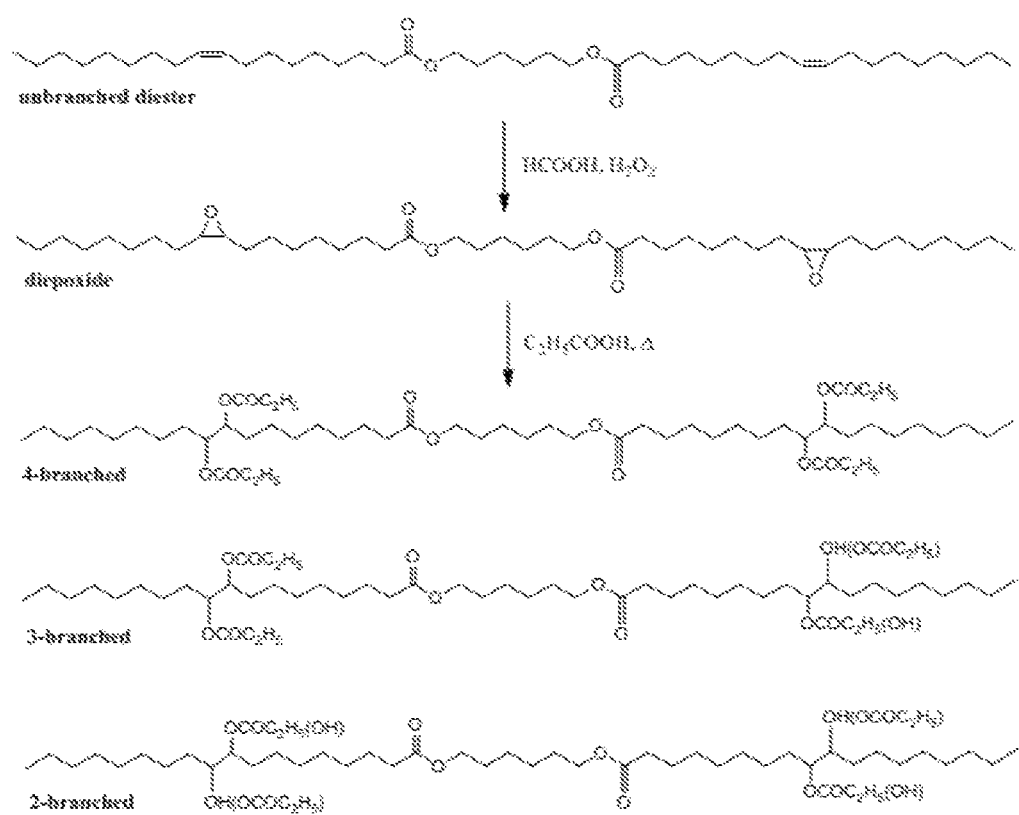
FIG. 2 shows a synthetic scheme corresponding to certain embodiments of making branched diesters disclosed herein.

The branched diesters were prepared via a 2-stage reaction as shown in FIG. 2 as Scheme 1. In the first stage of the reaction, the unsaturated 18-6-18 base diester was converted into a diepoxide using in situ-generated peroxy acid. In the second stage of the reaction, the pure diepoxide was ring-opened with propanoic acid at temperatures previously optimized for similar compounds to give the 2-, 3-, and 4-branched diester derivatives. Note that although solvent (dichloromethane) was used in the first stage of this small scale reaction (i.e., in epoxidation) because of the convenience of faster reaction times and fewer side products that it presents, the epoxidation can be performed under solvent free conditions, particularly on larger scales suitable for industrial applications. In fact, Narine et al. have already disclosed an optimized ecofriendly and green solvent free method for the epoxidation of vegetable oil derivatives that can be easily adapted for the large scale epoxidation of polyunsaturated linear esters such as those described in the present disclosure. See U.S. Provisional Application No. 62/109,441, filed Jan. 29, 2015, and incorporated herein by reference.

The branched derivatives were subsequently obtained via a synthetic scheme that was also ecofriendly and green, incorporating a one pot solvent-free and catalyst free ring opening of the diepoxide, followed by in situ normal esterification. In the first part of this one pot reaction, the reactivity of the ring-strained epoxide moiety towards acid catalyzed ring opening reactions was exploited to give the 2-branched diester derivative. Subsequent in situ condensation reactions between the secondary OH groups formed upon ring opening and the excess propanoic acid, in addition to the elevated temperatures which facilitated the evaporation of water and, thus, the forward reaction, gave the higher branched diester derivatives (3- and 4-branched).

Figure 3:
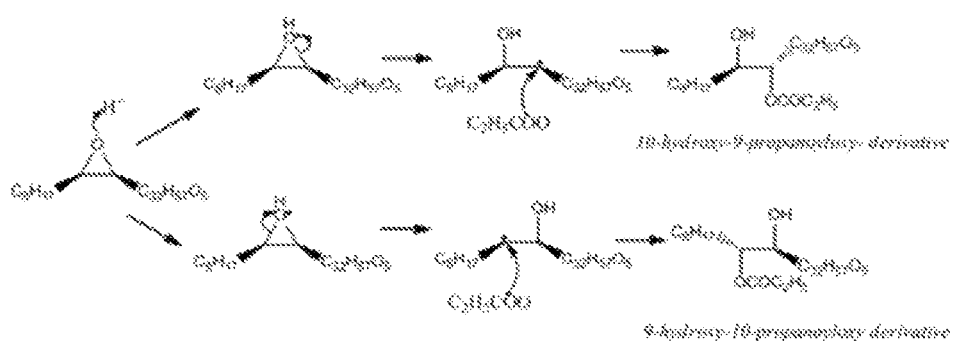
FIG. 3 shows a synthetic scheme corresponding to certain embodiments of making branched diesters disclosed herein.

Note that in the presence of acids, ring opening of the epoxide occurs via a nucleophilic substitution mechanism which is dependent on the degree of substitution of the electrophilic carbonyl centers; $S_N1$ occurs at the at the more substituted center to give the major product, while $S_N2$ occurs at the less substituted center to give the major product. In the diester of this work, all of the epoxy-carbonyl centers were equally substituted, resulting in nucleophilic attack at both the 9 and 10 positions to give a 1:1 mixture of the 9,10-positional isomers, which is shown in FIG. 3 as Scheme 2.

Synthesis of Diepoxide 6-(Oleoyloxy)hexyloleate (18-6-18) (70 g, 108 mmol) was weighed into a 500 mL round-bottom flask containing a magnetic stirrer bar, $CH_2Cl_2$ (100 mL) and formic acid (34 g, 88%) were added, and the reaction mixture cooled to 0° C. using an ice bath. $H_2O_2$ (54 g, 30%) was added dropwise to this cooled mixture with constant stirring. The reaction was then removed to room temperature and allowed to proceed until completed (as determined by TLC, approx. 5 h). Upon completion, the reaction mixture was diluted with dichloromethane (100 mL) and washed with water until neutral (4×200 mL) before being dried over anhydrous sodium sulphate and roto-evaporated to give the crude epoxide as a white solid. Pure epoxide (>99% purity) was obtained following column chromatography separation using ethyl acetate-hexanes (1:20 v/v) as the eluent.

6-(9,10-epoxyoctadecanoyloxy)hexyl-9,10-epoxyoctadecanoate, n6O$_2$; White solid (48 g, 62%); IR (ATR): 1727 (C=O) cm$^{-1}$, 846 (cis epoxide) cm$^{-1}$; $^1$H-NMR in CDCl$_3$ δ (ppm): 4.04-4.07 (4, t, O—C$\underline{H}_2$—), 2.88-2.92 (4, m, C—O—C$\underline{H}$—), 2.27-2.30 (4, t, O=CC$\underline{H}_2$—), 1.60-1.64 (8, m, O—CC$\underline{H}_2$—, O=CCC$\underline{H}_2$—), 1.46-1.49 (12, m, O—CCC$\underline{H}_2$—, C—O—CC$\underline{H}_2$—), 1.27-1.38 (40, m, C—C$\underline{H}_2$—), 0.86-0.89 (6, t, C—C$\underline{H}_3$). MS (ESI): calculated for C$_{42}$H$_{78}$O$_6$ 679, found m/z 702 ([M+Na]$^+$).

Synthesis of Branched Diesters

The diepoxide (n6O$_2$; 5 g, 7.4 mmol) was dissolved in excess propanoic acid (8 g) in a 100 mL round-bottom flask equipped with a magnetic stirrer bar. The reaction mixture was heated to 95° C. for the 2-branched diester derivative, and 120° C. for the 3- and 4-branched diester derivatives. The reaction was allowed to progress to completion (4-5 days as determined by TLC) with vigorous stirring under an atmosphere of nitrogen. Upon completion, the reaction mixture was quenched by pouring into water (50 mL). The organic layer was extracted with ethyl acetate (3×50 mL) and washed with saturated NaHCO$_3$ (1×50 mL) and water again until neutral (3×50 mL) before being dried over anhydrous sodium sulphate and concentrated on the roto-evaporator to afford the crude products as viscous orange oils. Pure 2-, 3- and 4-branched diesters (purity 95%) were isolated as colorless oils following column chromatography separation using (1:5 v/v), (1:5 v/v) and (1:10 v/v) ethyl acetate-hexanes as the eluting solvents, respectively.

6-((9,10-(dipropanoyloxy)octadecanoyloxy)hexyl-9,10-(dipropanoyloxy)-octadecanoate, 4-branched; colourless oil (2.2 g, 32%); $^1$H-NMR in CDCl$_3$ δ (ppm): 4.97-4.99 (4, t, O—C$\underline{H}$COR), 4.01-4.04 (4, t, O—C$\underline{H}_2$—), 2.29-2.34 (8, m, O=CC$\underline{H}_2$CH$_3$), 2.23-2.26 (4, t, O=CC$\underline{H}_2$—), 1.55-1.61 (8, m, O—CC$\underline{H}_2$—, O=CCC$\underline{H}_2$—), 1.47 (8, m, O—CHC$\underline{H}_2$—), 1.33-1.36 (4, m, O—CCC$\underline{H}_2$—), 1.22-1.24 (40, m, C—C$\underline{H}_2$—), 1.10-1.13 (12, t, O=CCC$\underline{H}_3$), 0.83-0.86 (6, t, C—C$\underline{H}_3$). MS (ESI): calculated for C$_{54}$H$_{98}$O$_{12}$ 939, found m/z 957 ([M+NH$_4$]$^+$).

6-((9(10)-hydroxy-10(9)-propanoyloxy)octadecanoyloxy)hexyl-9,10-(dipropanoyloxy)octadecanoate, 3-branched; colourless oil (2.77 g, 43%); $^1$H-NMR in CDCl$_3$ δ (ppm): 4.98-5.00 (2, t, O—C$\underline{H}$COR), 4.80-4.83 (1, in, O—C$\underline{H}$C(OH)), 4.02-4.05 (4, t, O—C$\underline{H}_2$—), 3.56 (1, m, C$\underline{H}$(OH)), 2.29-2.37 (6, m, O=CC$\underline{H}_2$CH$_3$), 2.25-2.28 (4, m, O=CC$\underline{H}_2$), 1.69 (b.s., O$\underline{H}$), 1.60-1.61 (8, m, O—CC$\underline{H}_2$—, O=CCC$\underline{H}_2$—), 1.48 (6, m, O—CHC$\underline{H}_2$—), 1.33-1.41 (6, m, O—CCC$\underline{H}_2$—, (HO)CC$\underline{H}_2$—), 1.23-1.28 (40, m, C—C$\underline{H}_2$—), 1.10-1.16 (9, m, O=CCC$\underline{H}_3$), 0.84-0.87 (6, t, C—C$\underline{H}_3$). MS (ESI): calculated for C$_{51}$H$_{94}$O$_{11}$ 883, found m/z 922 ([M+K]$^+$).

6-((9(10)-hydroxy-10(9)-propanoyloxy)octadecanoyloxy)hexyl-10(9)-hydroxy-9(10)-(propanoyloxy)octadecanoate, 2-branched; colourless oil (1.2 g, 19%); $^1$H-NMR in CDCl$_3$ δ (ppm): 4.81-4.84 (2, m, O—C$\underline{H}$C(OH)), 4.04-4.06 (4, t, O—C$\underline{H}_2$—), 3.56-3.59 (2, m, C$\underline{H}$(OH)), 2.34-2.38 (4, q, O=CC$\underline{H}_2$CH$_3$), 2.26-2.29 (4, dt, O=CC$\underline{H}_2$—), 1.61-1.63 (8, m, O—CC$\underline{H}_2$—, O=CCC$\underline{H}_2$—), 1.49 (b.s., O$\underline{H}$), 1.41-1.46 (4, m, O—CHC$\underline{H}_2$—), 1.34-1.40 (8, in, O—CCC$\underline{H}_2$—, (HO)CC$\underline{H}_2$—), 1.25-1.29 (40, in, C—C$\underline{H}_2$—), 1.14-1.17 (6, m, O=CCC$\underline{H}_3$), 0.86-0.88 (6, dt, C—C$\underline{H}_3$). MS (ESI): calculated for C$_{48}$H$_{90}$O$_{10}$ 827, found m/z 850 ([M+Na]$^-$).

Results and Discussion
Structure Characterization

Figure 4:
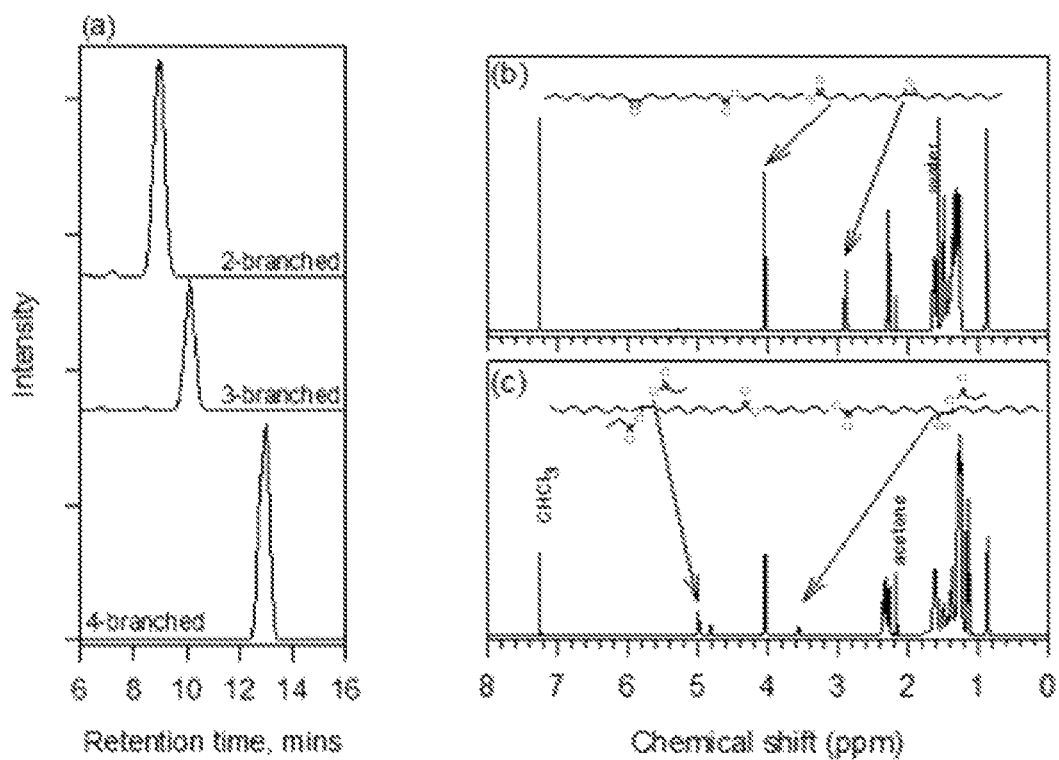
FIG. 4 shows: (a) HPLC curves for certain branched diesters; (b) the $^1$H NMR spectrum for the diepoxide; and (c) the $^1$H NMR spectrum for the 3-branched diester.

All of the branched diesters disclosed herein are novel; their syntheses and characterization are presented for the first time. The purity of each of the branched diesters was determined from the HPLC experiments, and the structures of the diepoxide and branched diesters were confirmed from $^1$H-NMR and MS experiments. The HPLC curves showing the purity of the branched diesters are presented in FIG. 4a, and representative $^1$H-NMR spectra of the diepoxide and the 3-branched diester are given in FIGS. 4b and 4c, respectively. The full $^1$H-NMR spectra of all of the branched diesters are presented in the supporting information. Note that the purity of each of the branched diester was higher than 95%.

In the $^1$H-NMR spectrum of the diepoxide (FIG. 4b), the proton chemical shifts at 2.8 ppm and 4.05 ppm (arrows in FIG. 4b) were characteristic of the C—O—CH epoxide proton and the protons a to the ester group (OCOCH$_2$), respectively. These indicated the formation of the epoxide group and the structural integrity of the linear diester, respectively. The absence of the chemical shift at 5.2 ppm indicates that all of the unsaturated moieties were converted into epoxide groups, while the absence of chemical shifts at 3.6 and 2.4 ppm, characteristic of the CH—OH and CH$_2$—C=O protons, respectively, confirmed that no ring-opened side product(s) was present in the isolated diepoxide. In the branched diesters, and as shown by the arrows in FIG. 4c for the 3-branched diester, the proton chemical shifts ($\delta$) at 5.00 ppm was characteristic of the branched ester-group (i.e., the O=COCH tnethyne proton), while the shift at 4.05 ppm (O=COCH$_2$ methylene protons) confirmed that the linear ester backbone on the molecules remained intact. Other characteristic shifts of the branched diesters included the CH—OH shift at 3.4-3.5 ppm, and the absence of the epoxide proton shift at 2.8 ppm.

Figure 5:
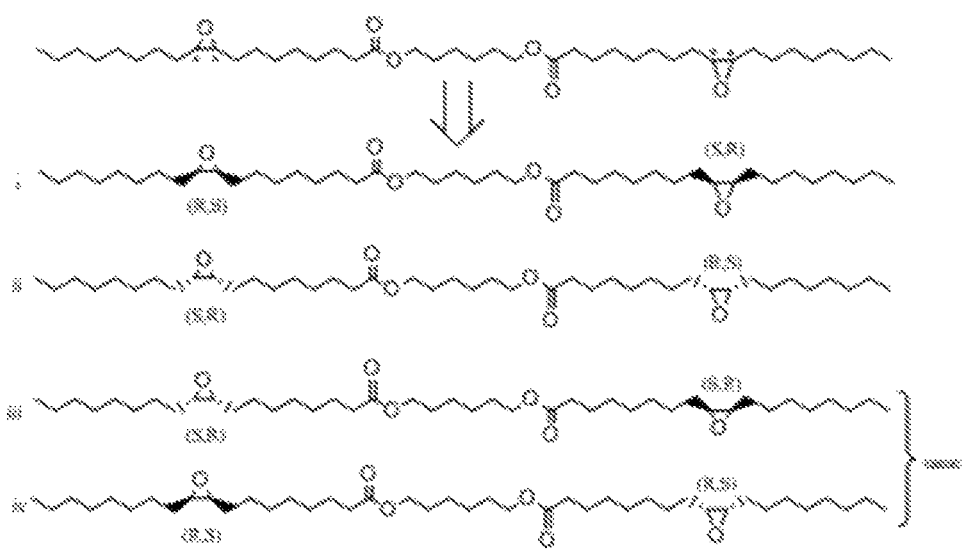
FIG. 5 shows stereoisomers of the diepoxide, 6-(9,10-epoxyoctadecanoyloxy)hexyl-9,10-epoxyoctadecanoate.
Figure 6:
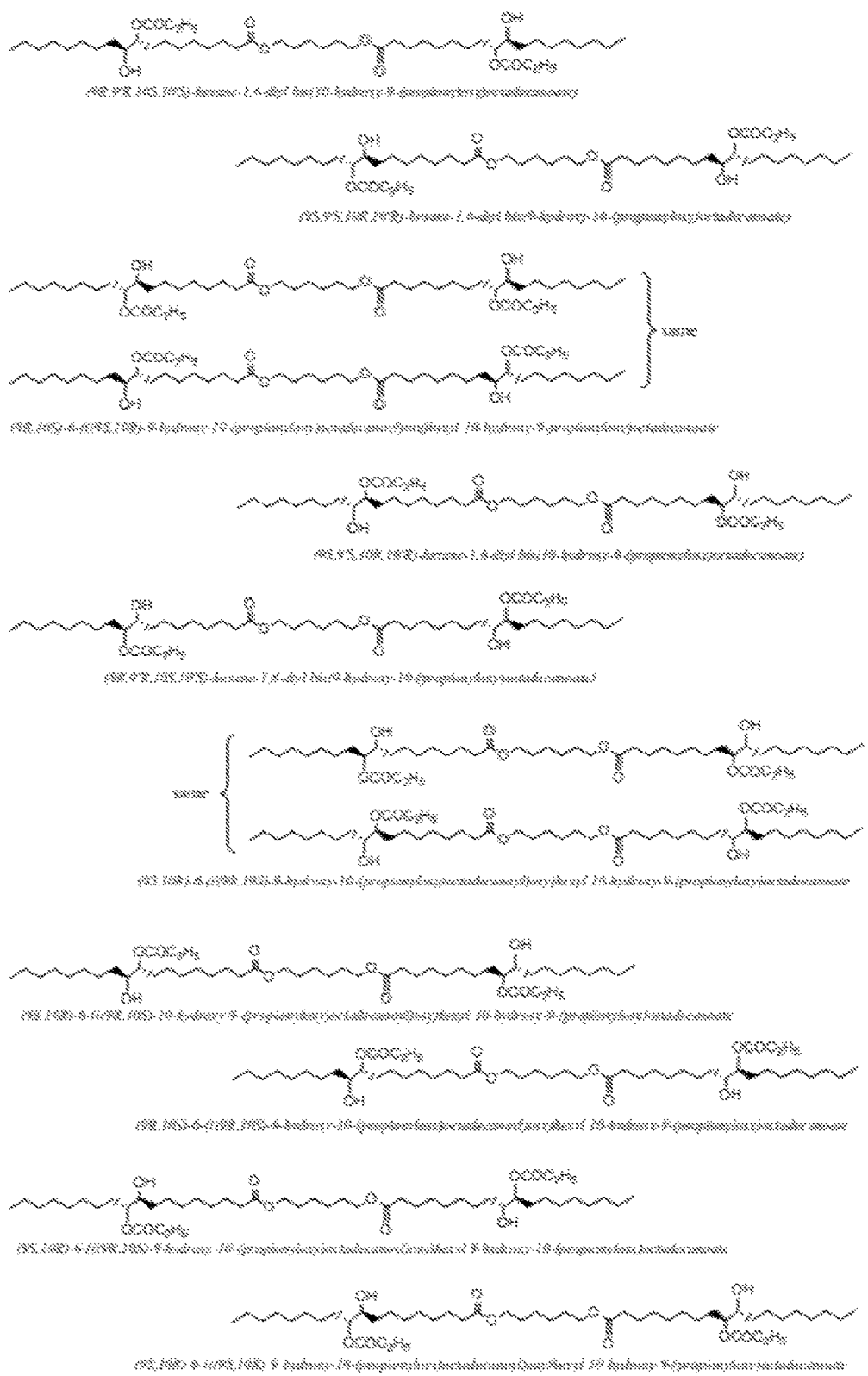
FIG. 6 shows certain positional- and stereo-isomers of the 2-branched diesters.
Figure 7:
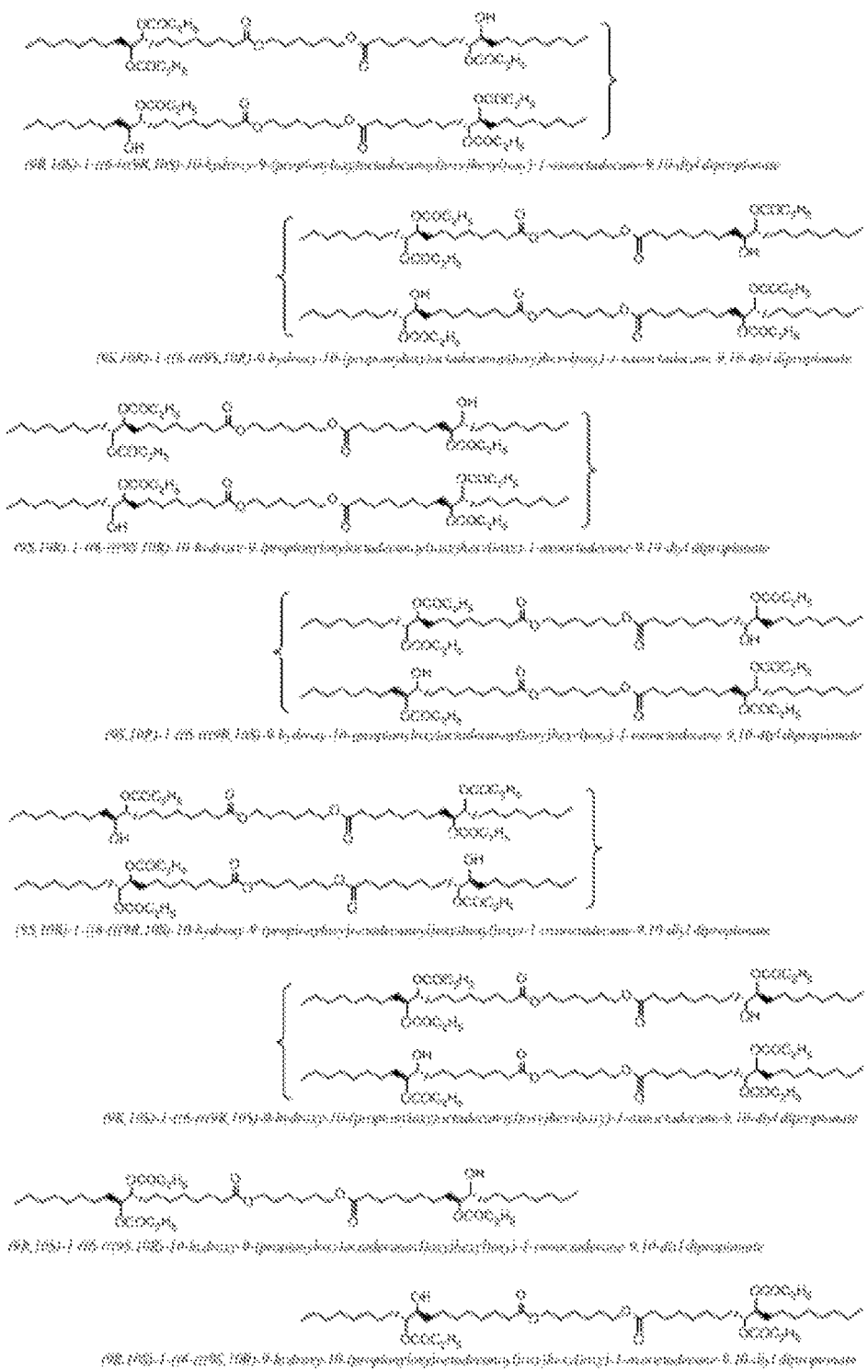
FIG. 7 shows certain positional- and stereo-isomers of the 3-branched diesters.
Figure 8:
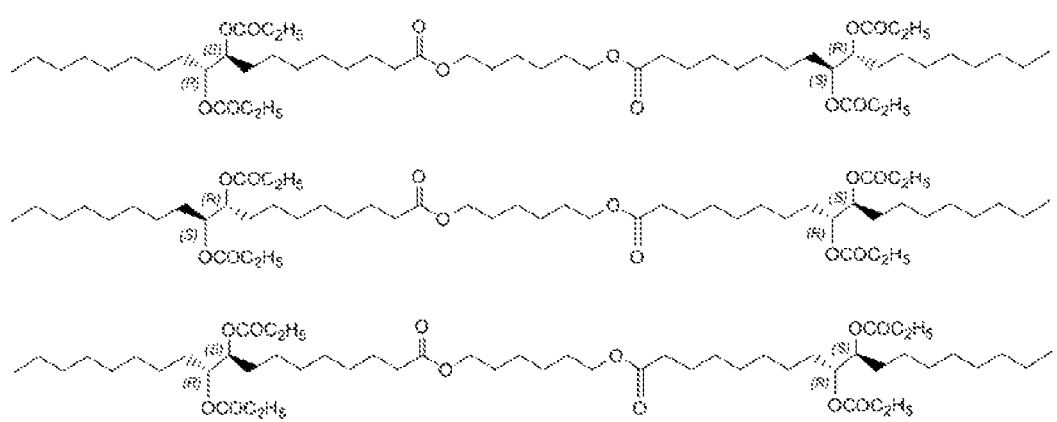
FIG. 8 shows stereoisomers of 4-branched diester, 6-((9,10-(dipropanoyloxy)-octadecanoyloxy)hexyl-9,10-(dipropanoyloxy)octadecanoate.

Epoxidation using performic acid proceeds with retention of stereochemistry, and introduces chirality at each of the carbon atoms of the epoxide moiety. Thus, epoxidation of the diepoxide results in a total of three stereoisomers, as shown in Scheme S.1, shown on FIG. 5, which, upon ring opening, gives a mixture of resulting stereoisomers for each of the branched derivatives. The isomeric inhomogeneity of each branched derivative was further exacerbated by the positional isomerism which occurs upon ring opening. Thus, 2-branched diesters will have comprised of a total of ten isomers which possessed both positional and stereo-isomerism (Scheme S.2, FIG. 6). In the higher branched derivatives, the number of positional isomers decreased with increasing esterification OH group such that the 3-branched derivative comprised of eight isomers possessing both positional and stereoisomerism (Scheme S.3, FIG. 7), and the 4-branched derivative comprised of three isomers which possessed only stereoisomerism (Scheme S.4, FIG. 8). Due to their similar polarities, these combinations of isomers were not readily separable with the chromatographic methods readily accessible in our labs (reversed-phase HPLC or gravity chromatography). Thus, their separation was not pursued in light of the anticipated difficulty and high cost of such purifications if used at commercial scales. Note that the proton chemical shifts of stereoisomers are similar to each other.

Flow Behavior

Figure 9:
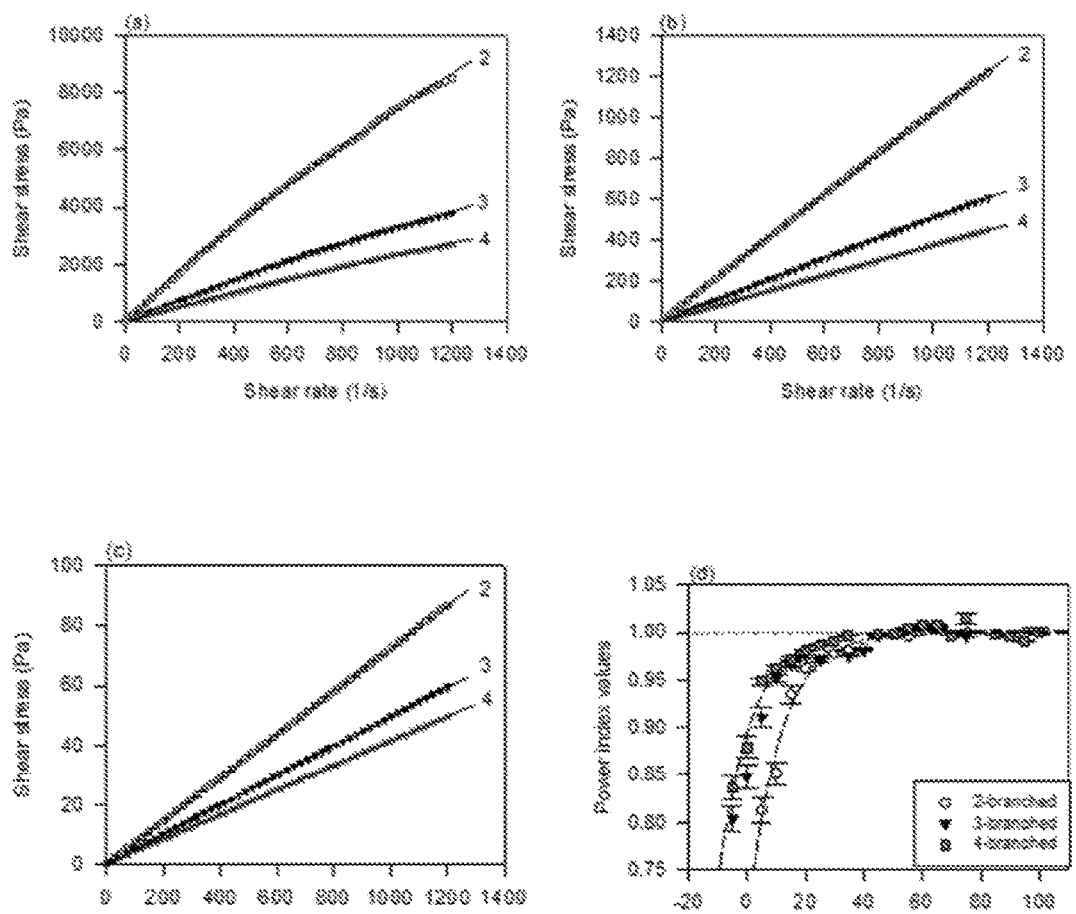
FIG. 9 shows the shear rate-shear stress curves of branched 18-6-18 diesters obtained at (a) 0° C., (b) 25° C., and (c) 75° C.; number of branches are reported on each curve; solid lines are fits to the Hierschel-Bulkley model (d) Herschel-Bulkley-derived power indices of branched diesters as functions of temperature; dashed lines are guides for the eyes.

The shear rate-shear stress curves obtained for the branched diesters at select temperatures (0, 25, 75° C.) are presented in FIG. 9a-c. All of the branched diesters were well fitted to the Herschel-Bulkley model (solid lines, FIG. 9a-c; R2>0.9985) with yield stress values of less than 0.055±0.020 Pas. The power law values derived from these fits are presented in FIG. 9d as a function of temperature for each diester.

FIG. 9d shows that the flow behavior of the branched diesters was shear thinning at low temperatures (0.80≤a<0.99 from −5 to 40° C.), progressing exponentially with increasing temperature (characteristic temperature 11.0±1.4° C., $R^2$≥0.9735) towards Newtonian. As can be seen in FIG. 9d, at any given temperature in the shear thinning region, the power index of the 2-branched diester was less than that of the 3-branched diester, which in turn was less than the 4-branched diester. That is, the branched diester derivatives were increasingly shear thinning with increasing number of OH groups and corresponding decreasing numbers of protuberant branched groups. Note that at the same temperatures, the difference between the power indexes of the 3- and 4-branched diesters was markedly smaller compared to the difference between the 2- and 3-branched diesters, indicating the prevailing effect of hydrogen bonding. Similar shear thinning flow behaviour (0.76≤a<0.99 for temperatures from −5 to 55° C.) have also been reported for branched diacid-derived jojoba-like diesters. The branched diacid-derived diesters were also increasingly shear thinning with increasing numbers of OH groups and decreasing branching.

These results may be understood in terms of the total intermolecular interactions and mass transfer limitation considerations. Shear thinning occurs when the stress which dominates at low shear rates does not increase with shear rate as fast as the Newtonian viscous stress. This stress is the result of the weak intermolecular interactions which exists between the branched diesters. It is greatest in the 2-branched diesters because this compound has the most hydrogen bonding density. At higher shear rates, poor mass transfer limits the reformation of these intermolecular bonds which break with shearing.

Viscosity

Figure 10:
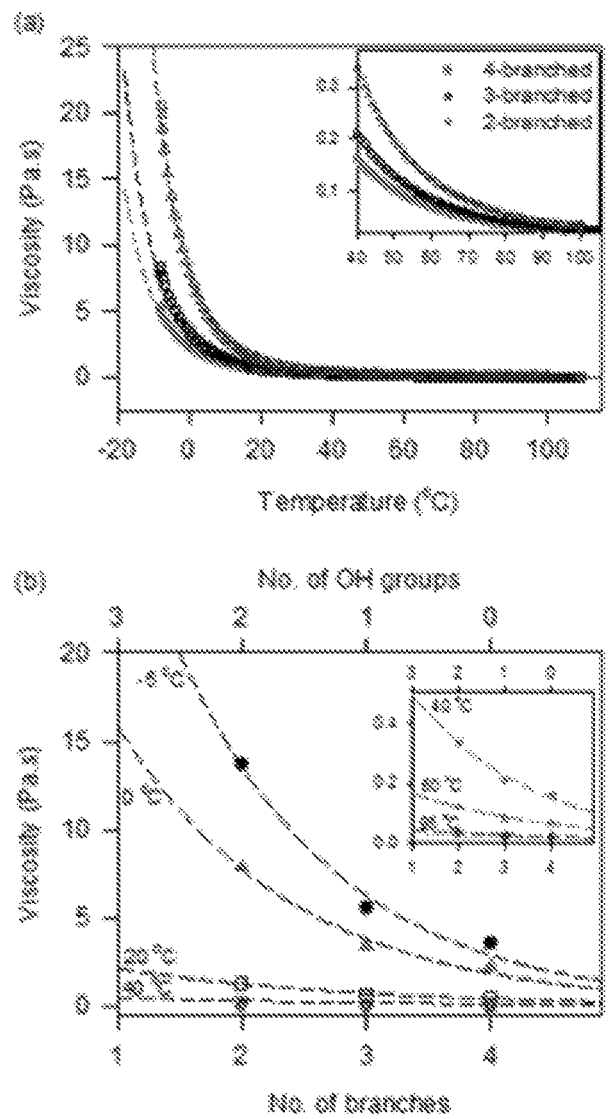
FIG. 10 shows viscosity versus temperature data of (a) branched diesters (data recorded at 3° C./min; inset in (a) is a zoom into the 40-100° C.); (b) and inset in (b) viscosity of the branched diesters at select temperatures as a function of number of ester branches (top x-axis) and number of OH groups (bottom x-axis). The measurement temperature in (b) are shown in front of each curve. Dashed lines are tentative exponential fits and serve as guides for the eye.

FIG. 10a shows the viscosity-temperature data of the branched derivatives of 18-6-18 diester. The viscosity of the branched diesters were all an order of magnitude higher than that of the unbranched 18-6-18 base diester (which spanned 0.006 to 0.5 Pa·s from 100 to 0° C.), outlining the dramatic effect of hydrogen bond density, mass and steric geometric hindrance (bulkiness) associated with the introduction of the branched ester groups. Amongst the branched diesters, increasing hydrogen bonding was clearly the dominating factor influencing viscosity. At any given temperature, the viscosity of the 2-branched di ester was larger than that of the 3-branched diester, which in turn was greater than that of the 4-branched diester, a result directly linked to the number of hydroxyl groups of the branched derivatives (zero, one and two OH groups in the in the 4-, 3- and 2 branched diesters, respectively). This data indicate that the effect on the viscosity of hydrogen bonding density is measurable and significant.

This is further clarified in FIG. 10b which show the viscosity at example temperatures reported as a function of the number of branched groups and the number of OH groups. The seemingly exponential trends ($R^2$≥0.9525) of FIG. 10b is similar to what was observed for branched diacid-derived diesters with non-terminal OH groups, or alternately, possessing terminal acyl groups, confirming the predominant effect of hydrogen bond density over the small ester group.

Thermal Transition Behavior

Figure 11:
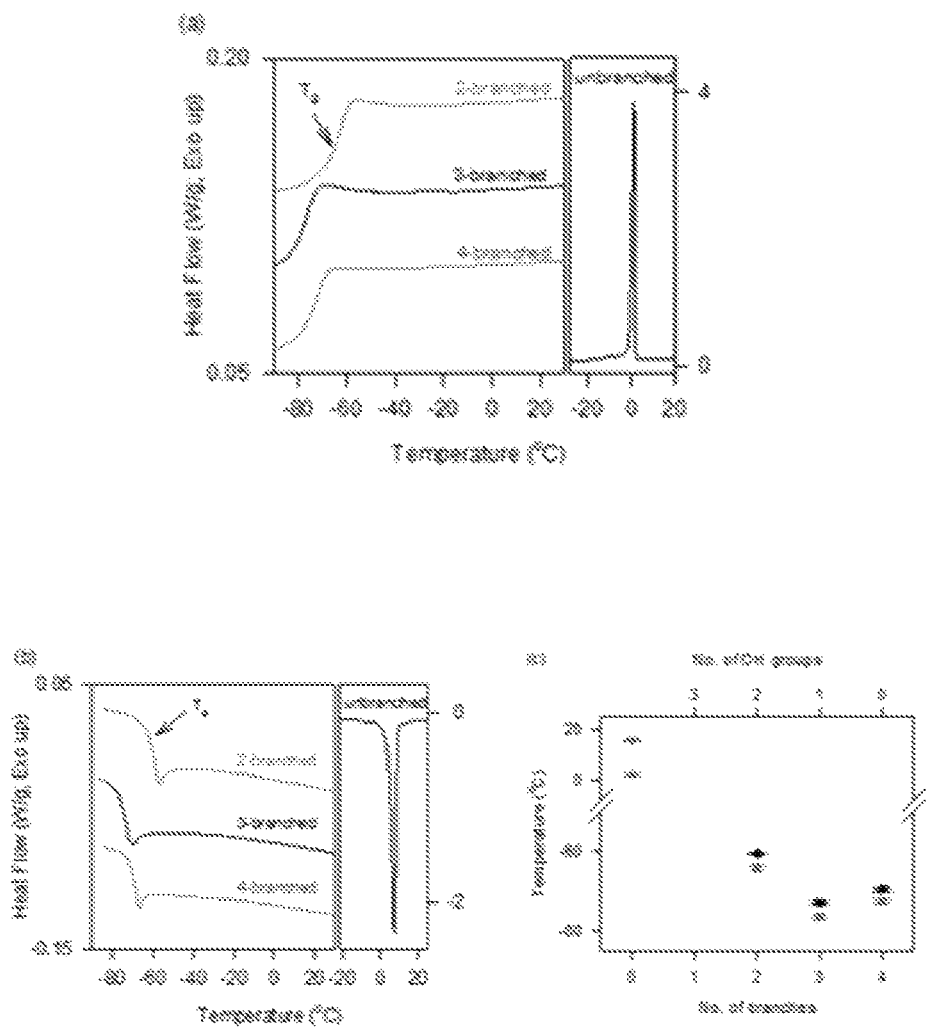
FIG. 11 shows the DSC (a) cooling and (b) heating thermograms, respectively, of the 18-6-18 base diester and its branched derivatives. (c) Glass transition temperature ($T_g$) during cooling (●) and heating (■) as a function of number of branches and number of hydroxyl groups per molecule. The crystallization onset (▲) and melting offset (▼) of the base unbranched diester are given for comparison purposes.

The thermal transition behavior of the branched 18-6-18 are presented in FIG. 11; FIG. 11a and FIG. 11b show the cooling and heating thermograms, respectively, and FIG. 11c present the characteristic temperatures versus the number of branched groups and hydroxyl groups. The cooling and heating thermograms and characteristic crystallization and melting temperatures of the unbranched base diester, 18-6-18 are also presented for comparison purposes.

FIG. 11a-b show that the thermal behavior of all the branched diesters was fundamentally different from that of the unbranched 18-6-18 diester. The unbranched diester crystallized with a sharp peak with an onset at 2.2±0.6° C. and a total enthalpy of 104.6±4.2 kJ/mol. These DSC characteristics of the 18-6-18 unbranched diester were previously shown to be those of the crystal phase having the triclinic subcell structure (so-called β-form). The thermograms of the branched diesters, on the other hand, showed only a glass transition which occurred at more than 60° C. below the crystallization temperature of the unbranched diester. The heating profiles of the branched diesters mirrored their cooling counterparts with a simple transformation from the glass to the liquid phase, and with no crystallization mediated by melt—a desirable behavior in materials for use in lubricant formulations.

The crystallization was completely suppressed in these internally-branched diesters in contrast to analogous diesters whose branched ester groups (also three carbons long) were terminal and in which crystallization was not fully suppressed and/or strong crystallization mediated by melt occurred upon heating. This indicates that the steric hindrance due to the protuberant ester branch on the fatty acid moiety was highly effective in disrupting the ability of the branched diester molecules to pack regularly in a crystal form. It is also likely that the difficulty of the branched molecules to pack was further exacerbated by the compositional inhomogeneity within each branched system due to the presence of positional- and/or stereo-isomers.

These results also contrast with those of analogous internally-branched monoesters—with similar total carbon chain length (44 C) and similar branched groups (propyl esters)—in which crystallization was not fully suppressed and/or in which recrystallization from the melt was promoted by the hydrogen bonding present in the 2- and 3-branched derivatives. This indicated that the second 'extra' ester group along the aliphatic backbone of the molecule introduced enough steric hindrance or "bulkiness" to suppress the crystallization completely. Note that similar steric hindrance between the aliphatic chain moieties of unbranched esters also accounts for the difference of ~15° C. in the crystallization temperature of the unbranched jojoba-like diester compared to unbranched jojoba-like monoester with similar chain length.

FIG. 11c shows that the glass transition of the 2-branched diester which has two OH groups occurred at the highest temperature ($T_g$=−60.5±0.3° C.). The addition of a branch— and the associated removal of an OH group—to give the 3-branched diester resulted in a decrease in $T_g$ by 12° C. ($T_g$=−72.9±0.5° C.). Generally, $T_g$ increases with increasing viscosity. As was shown in the preceding section, the viscosity of the branched diesters increased exponentially with increasing hydrogen bond density, indicating that the reduction in $T_g$ with increasing branching was primarily due to decreased viscosity (338 mPas versus 162 mPas at 40° C. for 2- and 3-branched diesters, respectively) associated with reduction of hydrogen bond density. Similar decreases in $T_g$ with decreasing OH content have been reported for branched jojoba-like monoesters and diesters. In the 4-branched diester of this disclosure, the addition of the fourth group, and the associated removal of the last OH group (and therefore all hydrogen bonding), resulted in a small 2° C.) increase in the glass transition temperature ($T_g$=−69.5±0.5° C.) compared to the 3-branched diester. This indicates that in the absence of hydrogen bonding, mass transfer limitations due to increasing molecular mass/molecular bulkiness also contributes significantly towards the viscosity, and hence, $T_g$, of these branched diesters.

$T_g$ was determined by the competing influence of decreased OH content and mass transfer limitations which accompany increased branching. The crystallization was effectively suppressed due the combined influence of internal protuberant groups upon branching, and the intermolecular steric hindrance upon the introduction of additional ester groups along the linear backbone of the molecule (e.g. linear monoesters versus linear diesters) which affects the close packing of the linear aliphatic chain segments of individual ester molecules. Note that the latter alone was not sufficient to effectively suppress crystallization.

Implications

The flow properties of the branched diesters of this work are presented in Table 1 (below) alongside those of typical commercial lubricants (mineral oil, polyalphaolefin, isoalkyl adipate) and the best-performing representative bio-based lubricants from the literature. Polyalphaolefins (PAO) and isoalkyl adipates (e.g. di i-C13 adipate) are examples of synthetic biodegradable basestocks. The flow properties of a soybean oil basestock have also been included for comparison. JLEM and JLED in Table 1 refer to the jojoba-like mono- and diesters, respectively, reported by the TCBR research group.

Table 1 shows that of the commercial lubricating basestocks, polyalphaolefin (PAO) maintained its fluidity at the lowest temperature (−63° C.), but also had the lowest viscosity (17 cP at 40° C.). The pour points (PP) reported for the best-performing biobased alternatives in the literature are comparable to that of PAO, but the viscosity is higher overall, ranging from ~30 cP—two times that of PAO—to ~390 cP at 40° C. The increased number of ester groups and hydrogen bonding density where OH groups were introduced was responsible for the higher viscosity of the biobased polyesters compared to PAO. The latter possessed only the relatively weaker van der Waals interactions arising from its hydrocarbon-only structure. Note also that all of the compounds presented in Table 1, including the best low temperature performance alternatives found in the literature, possess a combination of the structural elements known to influence crystallization, namely: kinks along the aliphatic backbone such as ester groups or cis-double bonds, and branched chains close to the ends of the molecules and/or within the molecule.

Of the biobased polyesters listed in Table 1, all of the fully branched derivatives of the jojoba-like monoesters (JLEM) and jojoba-like diesters (JLED) with internal ester branches did not crystallize and presented glass transitions below −57° C. instead. The presence of OH groups alongside ester groups at the terminal position, such as in the case of the partial branching (i.e., 2- and 3-branched) of JLEMs with terminal double bonds (e.g. entries 10-11 in Table 1), was demonstrated to suppress crystallization effectively when the OH was terminal and the branched ester group was protuberant. In order to take advantage of the derivatives of partial branching of JLEMs having terminal double bonds for low temperature performance lubricants, it would be necessary to isolate the effective positional isomer from the mixtures—a not so easy nor economical task at commercial scales. Even then, as has been clearly demonstrated, the desired positional isomers experience, over time, intramolecular 1,2-acyl group migration in which the ester group switches position with the terminal OH groups forming a more stable but much less effective isomer(s) which experience lingering crystallization during cooling and/or strong recrystallizations mediated by melt upon heating. In contrast, the branching of the diester of this work, although resulting in mixtures of different isomers, was very effective in suppressing crystallization, including with partial branching (the 2- and 3-branched derivatives). This is because all of the branches were internal, and an intramolecular 1,2-acyl group migration, if any, would not affect the protuberant nature of the branches and, therefore, would not impact the thermal behavior of the mixture significantly. It is therefore likely that there would be no need to separate the positional isomers to keep the low temperature performance of the mixtures.

The viscosity of the jojoba-like branched mono- and di-esters, inclusive of the branched diesters of this work, presented in Table 1 extended from 43 cP to ~340 cP (at 40° C.) depending on the total chain length, number and position of OH groups present. This viscosity range is markedly larger than what was reported for the other biobased compounds listed in Table 1, including the branched diesters of the present work (162-338 cP at 40° C.). Table 1 also shows that the branched jojoba-like esters, even if they present similar low temperature performance (i.e., same $T_g$) as the branched derivatives of the present work, may present widely different viscosity. For example, the 2-branched 18-6-18 (entry 17 in Table 1) and the 2-branched JLEMs with 28 carbon atoms (entry 10 in Table 1) present similar $T_g$ (~64° C.), but viscosities of 338 cP and 290 cP at 40° C., respectively. This does not preclude the use of these branched JLEMs and JLEDs, including the branched diesters of this work, in dedicated different low temperature applications based on their different viscosity classifications. For example, based on ISO specifications (ISO 3448: 1992) (and assuming that the dynamic viscosity for the branched diesters of this work can be acceptably compared to kinematic viscosity), the 2-branched, 3-branched and 4-branched 18-6-18 diesters may be classified as ISO VG 320, ISO VG 220, and ISO VG 150 industry oil grades, respectively, for use in industrial gear and bearing lubricants.

These results indicate that crystallization in the linear aliphatic diesters of the 18-n-18 series with varying diol chain lengths, which all possess internal double bonds, may be similarly suppressed upon the introduction of internal protuberant branched ester groups.

The thermal and rheology results show that the branched 18-6-18 diesters of this work can be used in lubricant formulations with improved low temperature performance compared to present commercial alternatives, inclusive of biobased alternatives. Like the branched JLEMs and JLEDs previously reported by our research group, the branched 18-6-18 diesters of the present work can be prepared using solvent free and catalyst free chemistries. The absence of double bonds in these compounds is also expected to result in improved oxidative stability compared to the branched alternatives which contain carbon-carbon unsaturation such as, for example, entry 8 in Table 1. The branched derivatives of 18-6-18 diester also improve on the branched JLEMs and JLED reported previously by our research group in that they can be used to formulate lubricants with similar low temperature properties and more varied viscosity profiles. Furthermore, the diesters of this work show increased potential for use as low temperature alternatives without the need for the separation of the isomers or without concern for the effects of the acyl group migration between the α-OH and ester groups in the partially branched derivatives upon storage or during thermal processing.

TABLE 1

| Entry | Material | Total chain length[a] (carbons) | Structure | Pour Point[b], °C. | Viscosity, cP @ 40° C. |
|---|---|---|---|---|---|
| 1 | Mineral Oil[d] | | | −21 | 71[c] |
| 2 | PAO[d] | | 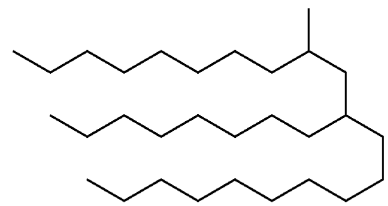 [SMILES: CCCCCCCCCCC(CCCCCCCC)CC(C)CCCCCCCC] | −63 | 17[c] |
| 3 | Soybean Oil[d] | 39 | 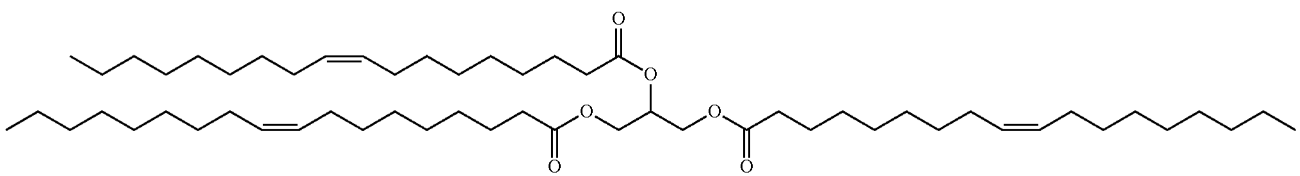 [SMILES: CCCCCCCC/C=C\CCCCCCCC(=O)OCC(COC(=O)CCCCCCC/C=C\CCCCCCCC)OC(=O)CCCCCCC/C=C\CCCCCCCC] | −9 | 32[c] |
| 4 | Di i-C13 adipate[d] | 32 | 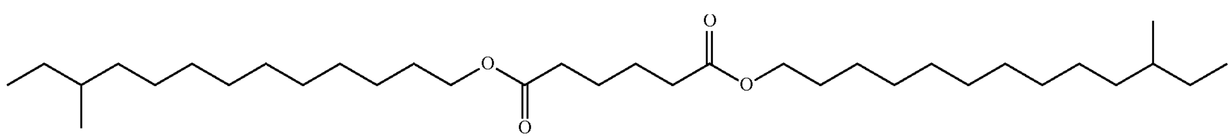 [SMILES: CCC(C)CCCCCCCCCCOC(=O)CCCCC(=O)OCCCCCCCCCCC(C)CC] | −54 | 27[c] |

TABLE 1-continued

| Entry | Material | Total chain length[a] (carbons) | Structure | Pour Point[b], °C. | Viscosity, cP @ 40° C. |
|---|---|---|---|---|---|
| 5 | Estolide[e] | 31 | 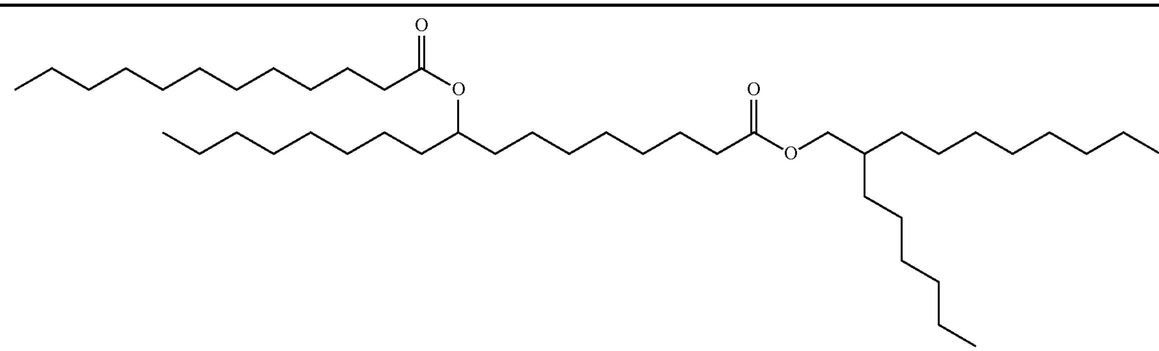 | −45 | 47[c] |
| 6 | Diester[f] | 35 | 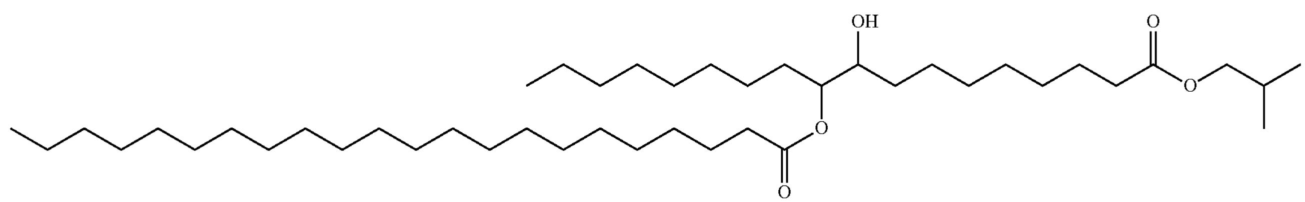 [SMILES: CCCCCCCCCCCCCCCCCCCCCC(=O)OC(CCCCCCCC)C(O)CCCCCCCC(=O)OCC(C)C] | −60 | 290 |
| 7 | Triester[g] | 35 | 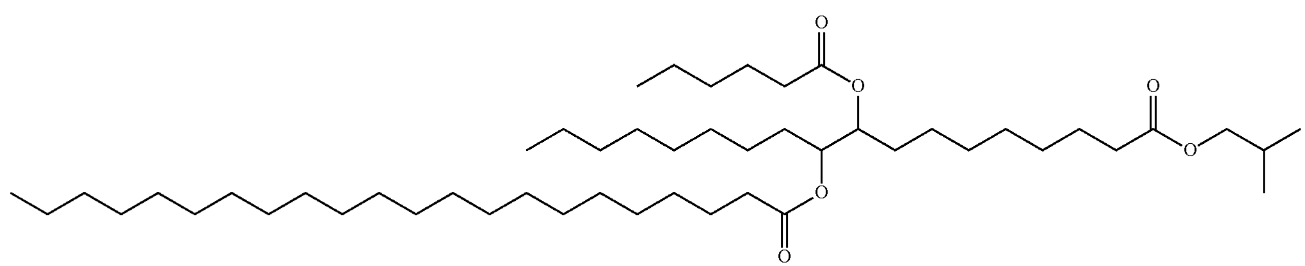 [SMILES: CCCCCCCCCCCCCCCCCCCCCC(=O)OC(CCCCCCCC)C(CCCCCCCC(=O)OCC(C)C)OC(=O)CCCCC] | −62 | — |

TABLE 1-continued

| Entry | Material | Total chain length[a] (carbons) | Structure | Pour Point[b], °C. | Viscosity, cP @ 40° C. |
|---|---|---|---|---|---|
| 8 | Diester[h] | 46 | 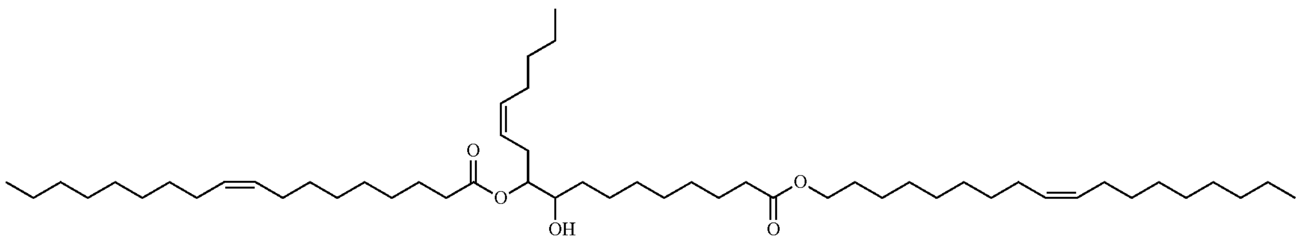 [SMILES: CCCC/C=C\CC(OC(=O)CCCCCCC/C=C\CCCCCCCC)C(O)CCCCCCCC(=O)OCCCCCCCC/C=C\CCCCCCCC] | −62 | 137[c] |
| 9 | JLEM[i] | 26 | 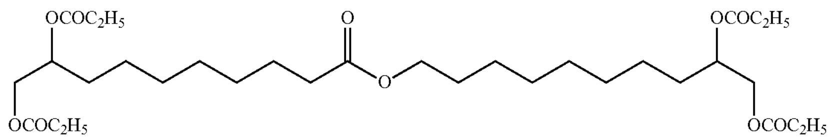 | <−90° C. | 43 |
| 10 | JLEM[i] | 28 | 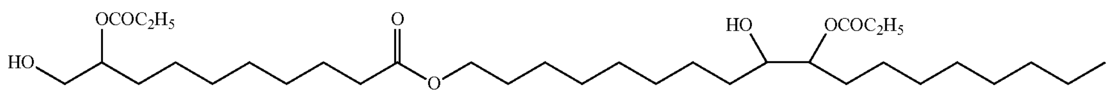 | −64 (T$_g$) | 290 |
| 11 | JLEM[i] | 28 | 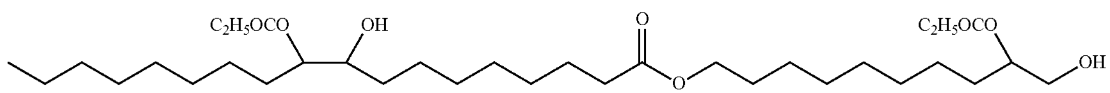 | −63 (T$_g$) | 232 |
| 12 | JLEM[i] | 31 | 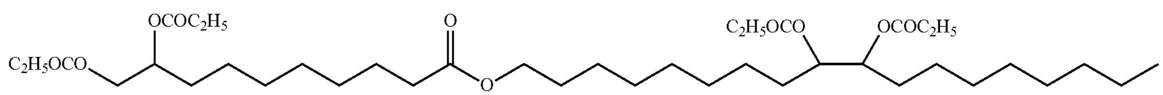 | −77 (T$_g$) | 84 |
| 13 | JLEM[i] | 31 | 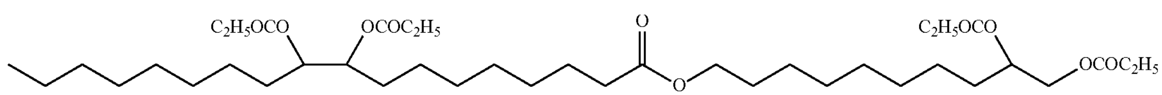 | −85 (T$_g$) | 66 |
| 14 | JLEM[i] | 36 | 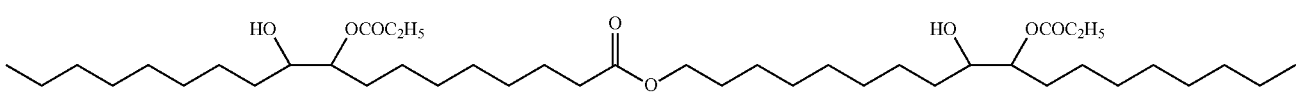 | −57 (T$_g$) | 391 |

TABLE 1-continued

| Entry | Material | Total chain length[a] (carbons) | Structure | Pour Point[b], °C | Viscosity, cP @ 40° C. |
|---|---|---|---|---|---|
| 15 | JLEM[j] | 36 | (structure) | −73 (T_g) | 130 |
| 16 | JLED[k] | 44 | (structure) | −72 (T_g) | 210 |
| 17 | JLED (this disclosure) | 42 | (structure) | −64 (T_g) | 338 |
| 18 | JLED (this disclosure) | 42 | (structure) | −77 (T_g) | 211 |
| 19 | JLED (this disclosure) | 42 | (structure) | −73 (T_g) | 162 |

In Table 1, the superscripts correspond to the following information. (a) Number of carbon atoms contained in the longest linear segment. (b) ASTM derived value for the last temperature at which a liquid will flow. (c) Dynamic viscosity was calculated from Kinematic viscosity using the relationship: Dynamic viscosity (cP)=Kinematic viscosity (cSt)×Density (g/cm$^3$), and assuming that density=1 g/cm$^3$. (d) As reported in literature. (e) As reported in literature. (f) As reported in literature. (g) As reported in literature. (h) As reported in literature. (i) Jojoba-like branched monoester. (j) Jojoba-like branched monoester. (k) Jojoba-like branched diester.

CONCLUSIONS

Novel aliphatic polyesters containing 2-, 3-, and 4-short chain (3-carbon) ester branches have been synthesized from 6-(oleoyloxy)hexyloleate (18-6-18) using a green ecofriendly approach which incorporated solvent-free and catalyst-free one pot chemistries. The viscosity of the base material increased by an order of magnitude upon branching due to the combined effects of increased mass, and integrated steric hindrances and hydrogen bonding. The internal nature of the sites of functionalization by enabling protruding ester branches and OH groups in the branched derivatives proved to be a structural feature that is instrumental in the resulting suppression of the crystallization independently of the degree of branching. The effectiveness of such branching was reflected in single glass transitions that appeared at very low temperatures, between −64° C. and −77° C. on both cooling and heating. The $T_g$ which is akin to the pour point depended on the number of branches and hydroxyl groups. The effect of hydrogen bond density on the viscosity was not only significant and measurable but also readily predictable as it scaled exponentially with the number of OH group at all temperatures in the liquid state.

The low temperature performance and viscosity profiles were obtained with mixtures comprising positional- and/or stereo-isomers. In fact there is no need for the separation of the isomers of the branched derivatives of 18-6-18 to obtain the desired excellent performance contrary to analogous previously studied derivatives of esters with terminal functionality, where a terminal position of the ester group in partially branched derivatives resulted in very poor performance of the material. Furthermore, the possible migration of the acyl chain which switches position with the OH group upon storage would not alter the phase trajectories in the partially branched derivatives of 18-6-18 as it did in their counterparts with terminal functionality.

Overall, the branched diesters of this disclosure presented thermal transition and viscosity profiles which are superior to existing analogous bio-based materials, making them suitable as green alternatives for high performance lubricant formulations.

REFERENCES

1. Nagendramma, P.; Kabel, S., Development of ecofriendly/biodegradable lubricants: An overview. *Renewable and Sustainable Energy Reviews* 2012, 16, 764-774.
2. Knothe, G.; Steidley, K. R., Lubricity of components of biodiesel and petrodiesel. The origin of biodiesel lubricity. *Energy & Fuels* 2005, 19, 1192-1200.
3. Meier, M. A.; Metzger, J. O.; Schubert, U. S. Plant oil renewable resources as green alternatives in polymer science. *Chemical Society Reviews* 2007, 36, 1788-1802.
4. Saurabh, T.; Patnaik, M.; Bhagt, S.; Renge, V. Epoxidation of vegetable oils: a review. *International Journal of Advanced Engineering Technology* 2011, 2, 491-501.
5. Anastas, P.; Eghbali, N. Green Chemistry: Principles and Practice. *Chemical Society Reviews* 2010, 39.
6. Statistica Global production of vegetable oils from 2000/01 to 2014/15 (in million metric tons). http://www-.statista.com/statistics/263978/global-vegetable-oil-production-since-2000-2001/(accessed 22 Sep. 2015).
7. Mandaković, R. The Key Influences on the Croatian arket of Lubricants and Markets in the Region. *goriva i maziva* 2011, 50, 307-316.
8. Tocci, L., Raw Materials under Pressure. *Lubes 'n' Greases* Mar. 7, 2012, pp 14-18.
9. Statistica World production of major vegetable oils from 2000/2001 to 2014/2015, by oil type (in million metric tons). http://www.statista.com/statistics/263933/production-of-vegetable-oils-worldwide-since-2000/(accessed 22 Sep. 2015).
10. Schneider, M. P. Plant-oil-based lubricants and hydraulic fluids. *Journal of the Science of Food and Agriculture* 2006, 86, 1769-1780.
11. Rodrigues Jr, J. d. A.; Cardoso, F. d. P.; Lachter, E. R.; Estevão, L. R.; Lima, E.; Nascimento, R. S. Correlating chemical structure and physical properties of vegetable oil esters. *Journal of the American Oil Chemists' Society* 2006, 83, 353-357.
12. Knothe, G.; Steidley, K. R. Lubricity of Components of Biodiesel and Petrodiesel. The Origin of Biodiesel Lubricity. *Energy & Fuels* 2005, 19, 1192-1200.
13. Bouzidi, L.; Li, S.; Di Biase, S.; Rizvi, S. Q.; Narine, S. S. Lubricating and Waxy Esters. 4. Synthesis, Crystallization Behavior, Melt Behavior, and Flow Behavior of Linear Monoesters Incorporating 9-Decenol and 9-Decenoic Acid. *Industrial & Engineering Chemistry Research* 2013, 52, 2740-2749.
14. Sharma, B. K.; Erhan, S. Z. 23 Modified Vegetable Oils for Environmentally Friendly Lubricant Applications. Synthetics, Mineral Oils, and Bio-based Lubricants: *Chemistry and Technology* 2013, 385.
15. Bouzidi, L.; Li, S.; Di Biase, S.; Rizvi, S. Q.; Dawson, P.; Narine, S. S. Lubricating and Waxy Esters II: Synthesis, Crystallization, and Melt Behavior of Branched Monoesters. *Industrial & Engineering Chemistry Research* 2012, 51, 14892-14902.
16. Sharma, B. K.; Doll, K. M.; Erhan, S. Z. Ester hydroxy derivatives of methyl oleate: tribological, oxidation and low temperature properties. *Bioresource Technology* 2008, 99, 7333-7340.
17. Li, S.; Bouzidi, L.; Narine, S. S. Lubricating and Waxy Esters, V: Synthesis, Crystallization, and Melt and Flow Behaviors of Branched. Monoesters Incorporating 9-Decenol and 9-Decenoic Acid. *Industrial & Engineering Chemistry Research* 2014, 53, 12339-12354.
18. Hungerford, Z.; Beare, K. D.; Yuen, A. K. L.; Masters, A. F.; Maschmeyer, T. Controlling viscosity in methyl oleate derivatives through functional group design. *New J. Chem.* 2014, 38, 5777-5785.
19. Erhan, S. Z.; Asadauskas, S. Lubricant basestocks from vegetable oils. *Industrial Crops and Products* 2000, 11, 277-282,
20. Adhvaryu, A.; Erhan, S. Z.; Perez, J. M. Tribological studies of thermally and chemically modified vegetable oils for use as environmentally friendly lubricants. *Wear* 2004, 257, 359-367.
21. Castro, W.; Perez, J. M.; Erhan, S. Z.; Caputo, F. A study of the oxidation and wear properties of vegetable oils:

Soybean oil without additives. *Journal of the American Oil Chemists Society* 2006, 83, 47-52.
22. Fox, N. J.; Stachowiak, G. W. Vegetable oil-based lubricants—A review of oxidation. *Tribology International* 2007, 40, 1035-1046.
23. Lathi, P. S.; Mattiasson, B. Green approach for the preparation of biodegradable lubricant base stock from epoxidized vegetable oil. *Applied Catalysis B—Environmental* 2007, 69, 207-212.
24. Sharma, B. K.; Adhvaryu, A.; Liu, Z.; Erhan, S. Z. Chemical modification of vegetable oils for lubricant applications. *Journal of the American Oil Chemists' Society* 2006, 83, 129-136.
25. Schmidt, M. A.; Dietrich, C. R.; Cahoon, E. B. Biotechnological Enhancement of Soybean Oil for Lubricant Applications. in *Synthetics, mineral oils, and bio-based lubricants: chemistry and technology* Rudnick, L. R., Ed. CRC Press: Boca Raton, Fla. 2006, 389-398.
26. Kulkarni, R. D.; Deshpande, P. S.; Mahajan, S. U.; Mahulikar, P. P. Epoxidation of mustard oil and ring opening with 2-ethylhexanol for biolubricants with enhanced thermo-oxidative and cold flow characteristics. *Ind. Crop. Prod.* 2013, 49, 586-592.
27. Gamage, P. K.; O'Brien, M.; Karunanayake, L. Epoxidation of some vegetable oils and their hydrolysed products with peroxyformic acid-optimised to industrial scale. *Journal of the National Science Foundation of Sri Lanka* 2009, 37, 229-240.
28. Findley, T. W.; Swern, D.; Scanlan, J. T. Epoxidation of unsaturated fatty materials with peracetic acid in glacial acetic acid solution. *Journal of the American Chemical Society* 1945, 67, 412-414.
29. Javni, I.; Guo, A.; Petrovic, Z. The study of oxazolidone formation from 9,10-epoxyoctadecane and phenylisocyanate. *Journal of the American Oil Chemists' Society* 2003, 80, 595-600.
30. Hong, J.; Luo, Q.; Shah, B. K. Catalyst- and Solvent-Free "Click" Chemistry: A Facile Approach to Obtain Cross-Linked Biopolymers from Soybean Oil. *Biomacromolecules* 2010, 11, 2960-2965.
31. Biswas, A.; Sharma, B. K.; Willett, J. L.; Advaryu, A.; Erhan, S. Z.; Cheng, H. N. Azide Derivatives of Soybean Oil and Fatty Esters. *Journal of Agricultural and Food Chemistry* 2008, 56, 5611-5616,
32. Anastas, P.; Kirchhoff, M. Origins; Current Status, and Future Challenges of Green Chemistry. *Accounts of Chemical Research* 2002, 35, 686-694.
33. Koroly, J. E.; Niederhauser, W. D., Process for the epoxidation of esters of oleic and linoleic acids. U.S. Pat. No. 2,485,160.
34. Li, S.; Bouzidi, L.; Narine, S. S. Lubricating and Waxy Esters. 6. Synthesis and Physical Properties of (E)-Didec-9-enyl Octadec-9-enedioate and Branched Derivatives. *Industrial & Engineering Chemistry Research* 2014, 53, 20044-20055.
35. Raghunanan, L.; Narine, S. S. Influence of methylene spacer groups on thermal and flow properties of linear aliphatic polyol-derived esters. *Journal of Physical Chemistry B* (submitted).
36. Raghunanan, L.; Yue, J.; Narine, S. S. Synthesis and Characterization of Novel Diol, Diacid and Di-isocyanate from Oleic acid. *Journal of the American Oil Chemists' Society* 2013, (submitted for publication).
37. Raghunanan, L.; Narine, S. S. Influence of Structure on Chemical and Thermal Stability of Aliphatic Diesters. *The Journal of Physical Chemistry B* 2013, 117, 14754-14762.
38. Floros, M. C.; Narine, S. S. Latent Heat Storage Using Renewable Phase Change Materials: Saturated Diesters from Vegetable Oils. 2014.
39. Floros, M. C.; Narine, S. S. Latent Heat Storage Using Renewable Saturated Diesters as Phase Change Materials. *Energy* (submitted).
40. Santos, J. C. O.; Santos, I. M. G.; Souza, A. G.; Sobrinho, E. V.; Fernandes, V. J.; Silva, A. J. N. Thermoanalytical and rheological characterization of automotive mineral lubricants after thermal degradation. *Fuel* 2004, 83, 2393-2399.
41. Gan, L. H.; Goh, S. H.; Ooi, K. S. Kinetic studies of epoxidation and oxirane cleavage of palm olein methyl esters. *Journal of the American Oil Chemists' Society* 1992, 69, 347-351.
42. Campanella, A.; Fontanini, C.; Bananás, M. A. High yield epoxidation of fatty acid methyl esters with performic acid generated in situ. *Chemical Engineering Journal* 2008, 144, 466-475,
43. Pillai, P. K. S.; Li, S.; Bouzidi, L.; Narine, S. S. Solvent Free Synthesis of Polyols from 1-Butene Metathesized Palm Oil for Use in Polyurethane Foams (unpublished).
44. Narine, S. S.; Pillai, P. K. S.; Li, S.; Bouzidi, L. Metathesized triacylglycerol green polyols from palm oil for use in polyurethane applications and their related physical properties. U.S. Patent Application No. 62/109, 441, filed Jan. 29, 2015.
45. Carey, F. A.; Sundberg, R. J., Oxidations. in *Advanced Organic Chemistry*, Springer: 1990; 615-675.
46. Parashar, R. K. Reaction mechanisms in organic synthesis. John Wiley & Sons: 2013.
47. Parker, N M R determination of enantiomeric purity. *Chemical Reviews* 1991, 91, 1441-1457.
48. Brown, E.; Jaeger, H. M. Through thick and thin, *Science* 2011, 333, 1230-1231,
49. Craven, R. J.; Lencki, R. W. Polymorphism of acylglycerols: a stereochemical perspective. *Chemical Reviews* 2013, 113, 7402-7420.
50. Craven, R. J.; Lencki, R. W. Crystallization, polymorphism, and binary phase behavior of model enantiopure and racemic 1,3-diacylglycerols. *Crystal Growth Design* 2011, 11, 1566-1572.
51. Craven, R. J.; Lencki, R. W. Crystallization, polymorphism, and binary phase behavior of model enantiopure and racemic triacylglycerols. *Crystal Growth & Design* 2011, 11, 1723-1732.
52. Bouzidi, L.; Li, S.; Di Biase, S.; Rizvi, S. Q.; Narine, S. S. Lubricating and waxy esters, I. Synthesis, crystallization, and melt behavior of linear monoesters. *Chemistry and Physics of Lipids* 2012, 165, 38-50.
53. Debenedetti, P. G.; Stillinger, F. H. Supercooled liquids and the glass transition. *Nature* 2001, 410, 259-267.
54. Cermak, S. C.; Bredsguard, J. W.; Roth, K. L.; Thompson, T.; Feken, K. A.; Isbell, T. A.; Murray, R. E. Synthesis and physical properties of new coco-oleic estolide branched esters. *Industrial Crops and Products* 2015, 74, 171-177.
55. Salimon, J.; Salih, N. Preparation and Characteristic of 9,10-Epoxyoleic Acid α-Hydroxy Ester Derivatives as Biolubricant Base Oil. *European Journal of Scientific Research* 2009b, 31, 265-272.
56. Salimon, J.; Salih, N.; Yousif, E. Chemically modified biolubricant basestocks from epoxidized oleic acid: Improved low temperature properties and oxidative stability. *Journal of Saudi Chemical Society* 2011a, 15, 195-201.

57. Salimon, J.; Salih, Abdullah, B. M. Diesters biolubricant base oil: synthesis, optimization, characterization, and physicochemical characteristics. *International Journal of Chemical Engineering* 2012, 2012.
58. Narine, S.; Li, S.; Mahdevari, A.; Bouzidi, L.; DiBiase, S. A.; Rizvi, S. Q., Esters for use as a base stock and in lubricant applications. U.S. Patent Application Publication No. 2014/0235517

The invention claimed is:

1. A compound of formula (I):

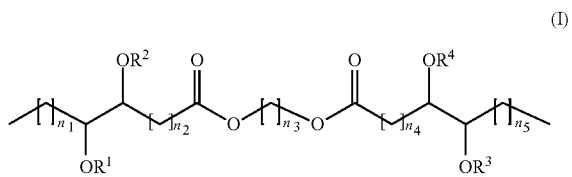

(I)

wherein:
R$^1$, R$^2$, R$^3$, and R$^4$ are independently a hydrogen atom or —C(O)—(C$_{1-6}$ alkyl);
n$_1$ and n$_5$ are independently an integer from 5 to 13;
n$_2$ and n$_4$ are independently an integer from 6 to 13; and
n$_3$ is an integer from 2 to 10.

2. The compound of claim 1, wherein one of R$^1$, R$^2$, R$^3$ or R$^4$ is a hydrogen atom.

3. The compound of claim 1, wherein one of R$^1$, R$^2$, R$^3$ or R$^4$ R$^1$ is —C(O)—(C$_{1-6}$ alkyl).

4. The compound of claim 3, wherein one of R$^1$, R$^2$, R$^3$ or R$^4$ is —C(O)—CH$_2$CH$_3$.

5. The compound of claim 1, wherein no more than two of R$^1$, R$^2$, R$^3$, and R$^4$ are a hydrogen atom.

6. The compound of claim 1, wherein no more than one of R$^1$, R$^2$, R$^3$, and R$^4$ are a hydrogen atom.

7. The compound of claim 1, wherein none of R$^1$, R$^2$, R$^3$, and R$^4$ is a hydrogen atom.

8. The compound of claim 1, wherein n$_3$ is 2, 4, 6, 8, or 10.

9. The compound of claim 1, wherein n$_2$ is 7, 9, 11, or 13.

10. The compound of claim 1, wherein n$_4$ is 7, 9, 11, or 13.

11. The compound of claim 1, wherein n$_1$ is 5 or 7.

12. The compound of claim 1, wherein n$_5$ is 5 or 7.

13. A composition comprising one or more compounds of claim 1.

14. The composition of claim 13, which comprises:
a first compound of formula (I), wherein R$^1$, R$^2$, R$^3$, and R$^4$ are —C(O)—(C$_{1-6}$ alkyl);
a second compound of formula (I), wherein one of R$^1$, R$^2$, R$^3$, and R$^4$ is a hydrogen atom, and the other three of R$^1$, R$^2$, R$^3$, and R$^4$ are —C(O)—(C$_{1-6}$ alkyl); and
a third compound of formula (I), wherein two of R$^1$, R$^2$, R$^3$, and R$^4$ are a hydrogen atom, and the other two of R$^1$, R$^2$, R$^3$, and R$^4$ are —C(O)—(C$_{1-6}$ alkyl).

15. The composition of claim 14, which comprises:
a first compound of formula (I), wherein R$^1$, R$^2$, R$^3$, and R$^4$ are —C(O)—CH$_2$CH$_3$;
a second compound of formula (I), wherein one of R$^1$, R$^2$, R$^3$, and R$^4$ is a hydrogen atom, and the other three of R$^1$, R$^2$, R$^3$, and R$^4$ are —C(O)—CH$_2$CH$_3$; and
a third compound of formula (I), wherein two of R$^1$, R$^2$, R$^3$, and R$^4$ are a hydrogen atom, and the other two of R$^1$, R$^2$, R$^3$, and R$^4$ are —C(O)—CH$_2$CH$_3$.

16. The composition of claim 15, wherein the composition is a lubricant composition.

17. The composition of 16, further comprising mineral oil or a poly(alpha-olefin).

18. The composition of claim 17, wherein the composition is a fuel composition, such as a biodiesel composition.

19. A method of lubricating a surface, comprising:
providing a first surface and a second surface, which are in physical contact with each other; and
contacting the first surface and the second surface with a composition of claim 13 at a point where the surfaces are in physical contact with each other.

20. The method of claim 19, wherein at least one of the first surface or the second surface is the surface of a gear or bearing.

* * * * *